(12) United States Patent
Zushi et al.

(10) Patent No.: US 11,135,418 B2
(45) Date of Patent: Oct. 5, 2021

(54) CATHETER, SWITCHING DEVICE, AND METHOD FOR OPERATING CATHETER

(71) Applicant: TERUMO KABUSHIKI KAISHA, Tokyo (JP)

(72) Inventors: Yasunobu Zushi, Kanagawa (JP); Shinya Kusunoki, Ishikawa (JP); Shinichi Mizuno, Yamanishi (JP); Takanori Tominaga, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 261 days.

(21) Appl. No.: 16/138,579

(22) Filed: Sep. 21, 2018

(65) Prior Publication Data

US 2019/0022370 A1 Jan. 24, 2019

Related U.S. Application Data

(63) Continuation of application No. PCT/JP2017/011393, filed on Mar. 22, 2017.

(30) Foreign Application Priority Data

Mar. 24, 2016 (JP) ................................. 2016-060154

(51) Int. Cl.
*A61M 39/26* (2006.01)
*A61M 25/00* (2006.01)
(Continued)

(52) U.S. Cl.
CPC .......... *A61M 39/26* (2013.01); *A61M 25/007* (2013.01); *A61M 25/0028* (2013.01);
(Continued)

(58) Field of Classification Search
CPC .............. A61M 25/0028; A61M 39/22; A61M 25/007; A61M 25/0097; A61M 39/105;
(Continued)

(56) References Cited

U.S. PATENT DOCUMENTS 1,658,754 A * 2/1928 Wood .................. A61M 3/0283
604/32
5,466,228 A * 11/1995 Evans .................. A61M 39/223
137/625.47

(Continued)

FOREIGN PATENT DOCUMENTS

JP 2001-509697 A 7/2001

OTHER PUBLICATIONS

International Search Report and Written Opinion in PCT/JP2017/011393, dated May 23, 2017, 8 pages.

(Continued)

*Primary Examiner* — Theodore J Stigell
*Assistant Examiner* — Daniel Moore
(74) *Attorney, Agent, or Firm* — Foley & Lardner LLP

(57) ABSTRACT

A catheter includes: a first port; a second port; a first lumen communicating with the first port; a second lumen configured to selectively communicate with the first port and/or the second port; and a switching mechanism part selectively switchable between a first switching state in which the first port and the second lumen communicate with each other and a second switching state in which communication between the first port and the second lumen is blocked.

14 Claims, 16 Drawing Sheets

(51) Int. Cl.
    *A61M 39/22*     (2006.01)
    *A61M 39/10*     (2006.01)
    *A61M 39/24*     (2006.01)

(52) U.S. Cl.
    CPC ...... *A61M 25/0097* (2013.01); *A61M 39/105* (2013.01); *A61M 39/22* (2013.01); *A61M 39/24* (2013.01); *A61M 25/0043* (2013.01); *A61M 2039/229* (2013.01)

(58) Field of Classification Search
    CPC .............. A61M 39/24; A61M 25/0043; A61M 39/223; A61M 1/0058; A61M 1/0064; A61M 2039/226; A61M 2039/229; A61M 39/26
    See application file for complete search history.

(56) References Cited

U.S. PATENT DOCUMENTS 5,800,408 A * 9/1998 Strauss ............... A61M 25/007
                                            137/625.47
2016/0008569 A1     1/2016 Harding

OTHER PUBLICATIONS

Translation of the International Search Report in corresponding application No. PCT/JP2017/011393.
Translation of the Written Opinion of the International Searching Authority in corresponding application No. PCT/JP2017/011393.

\* cited by examiner

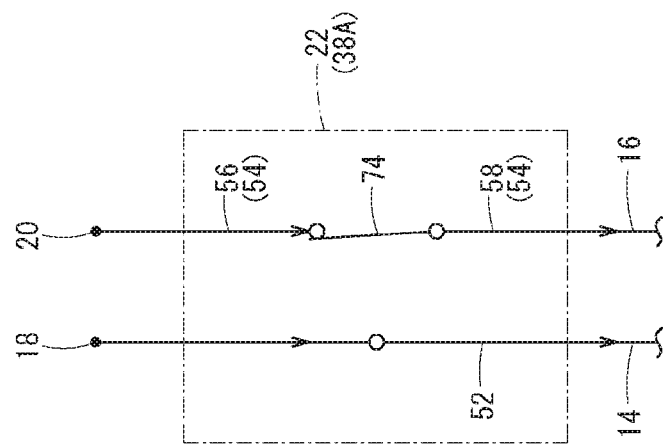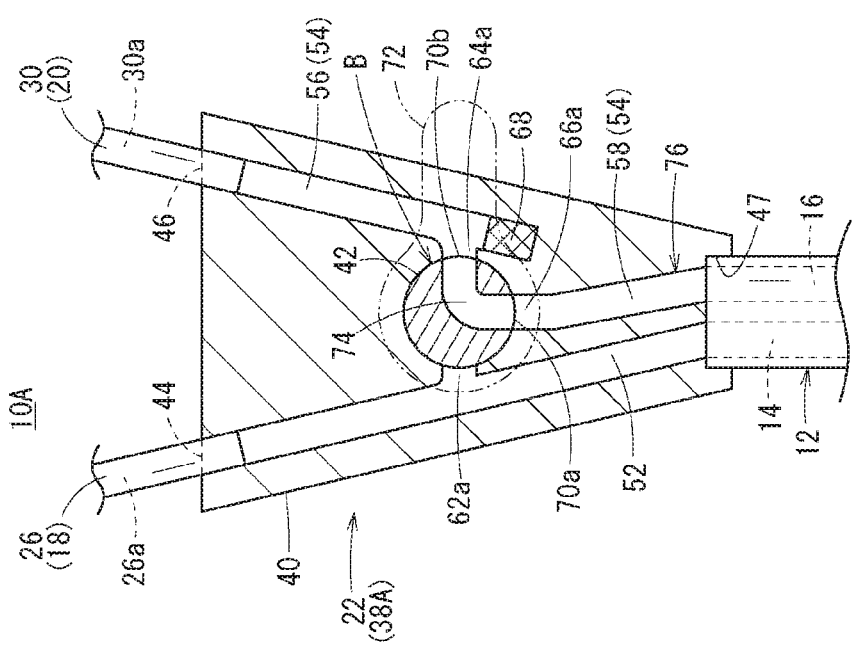

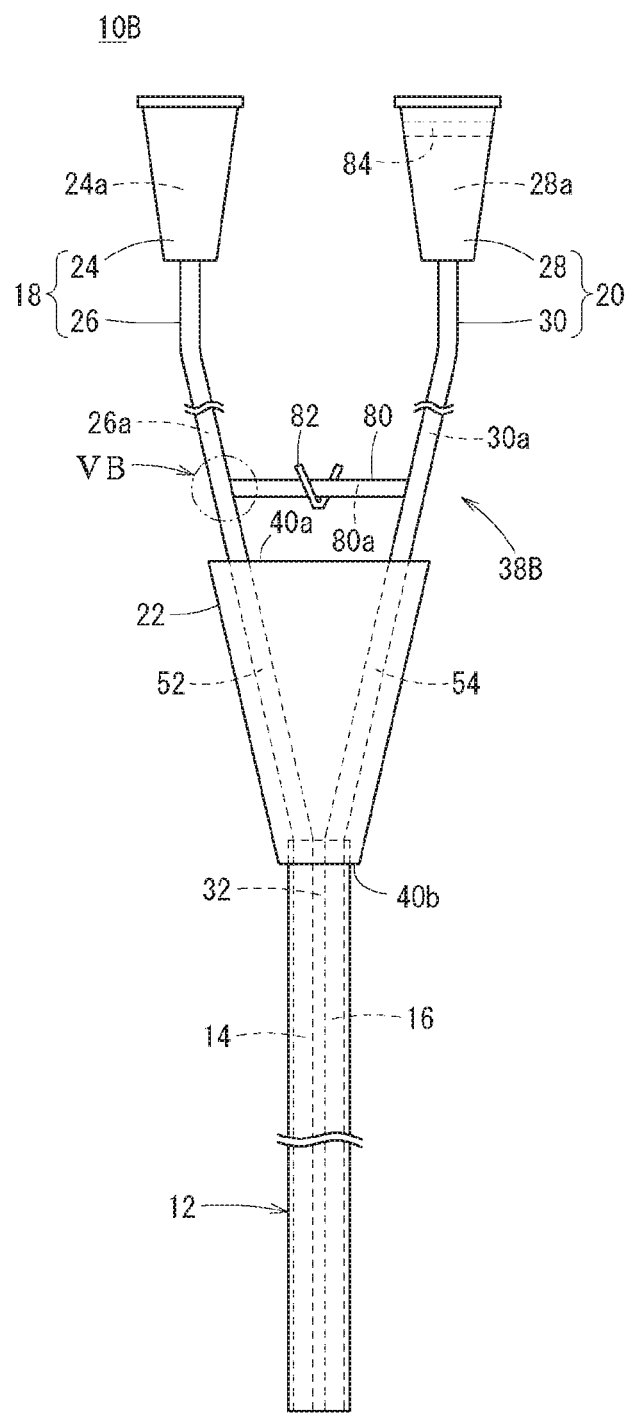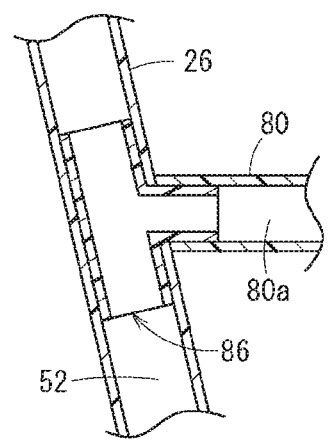

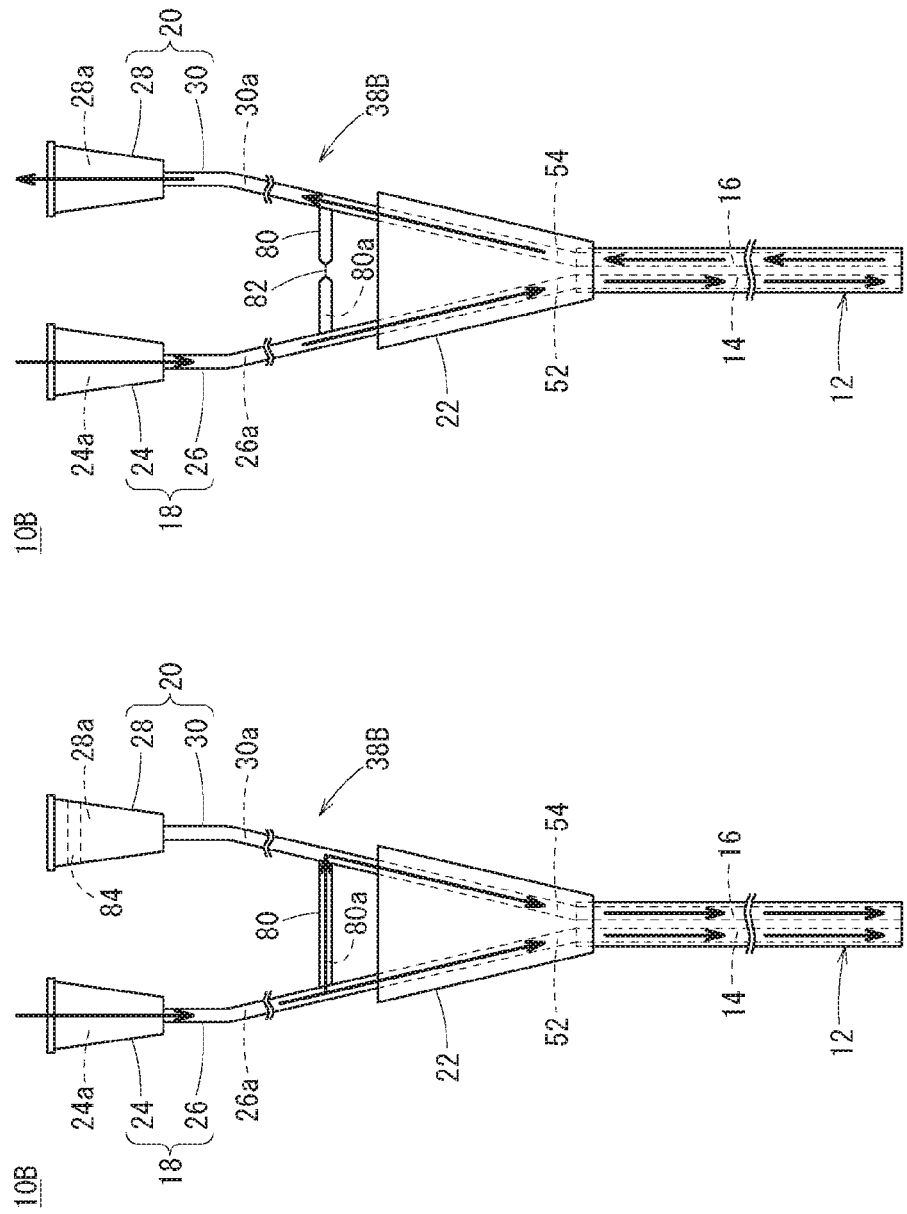

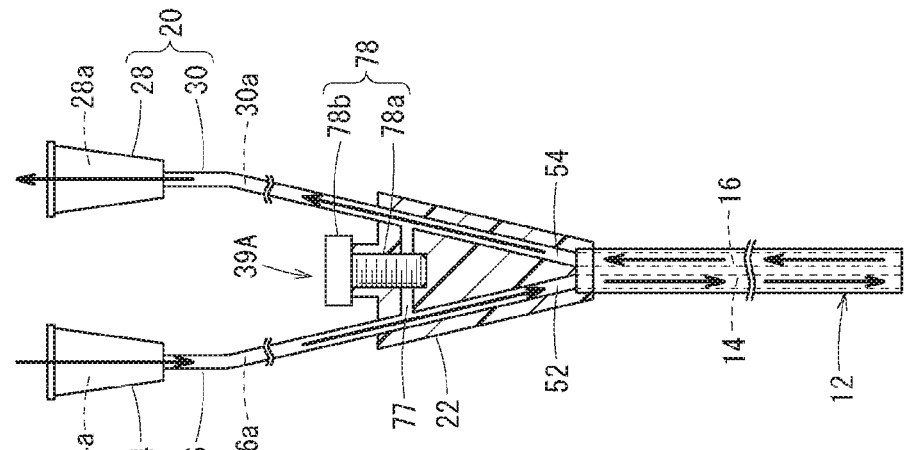
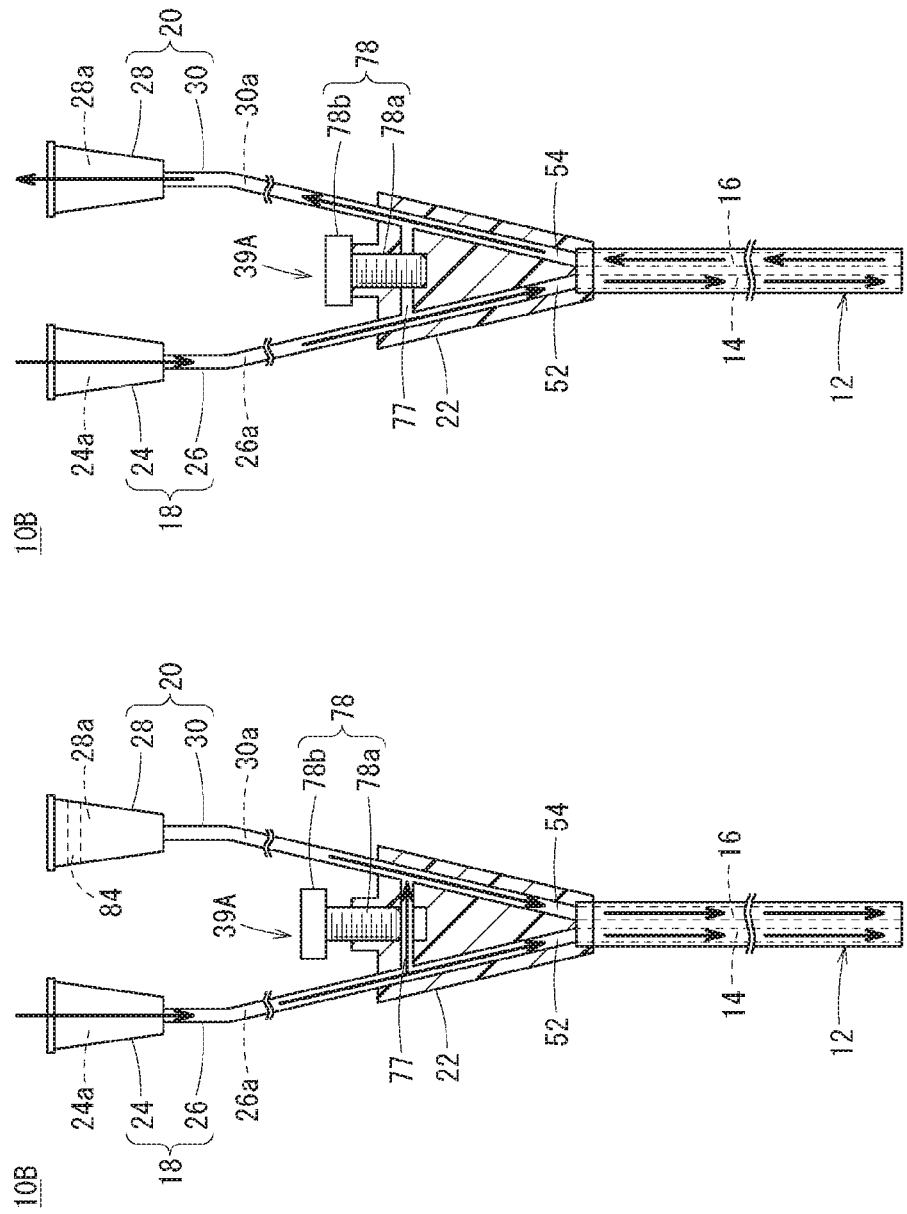

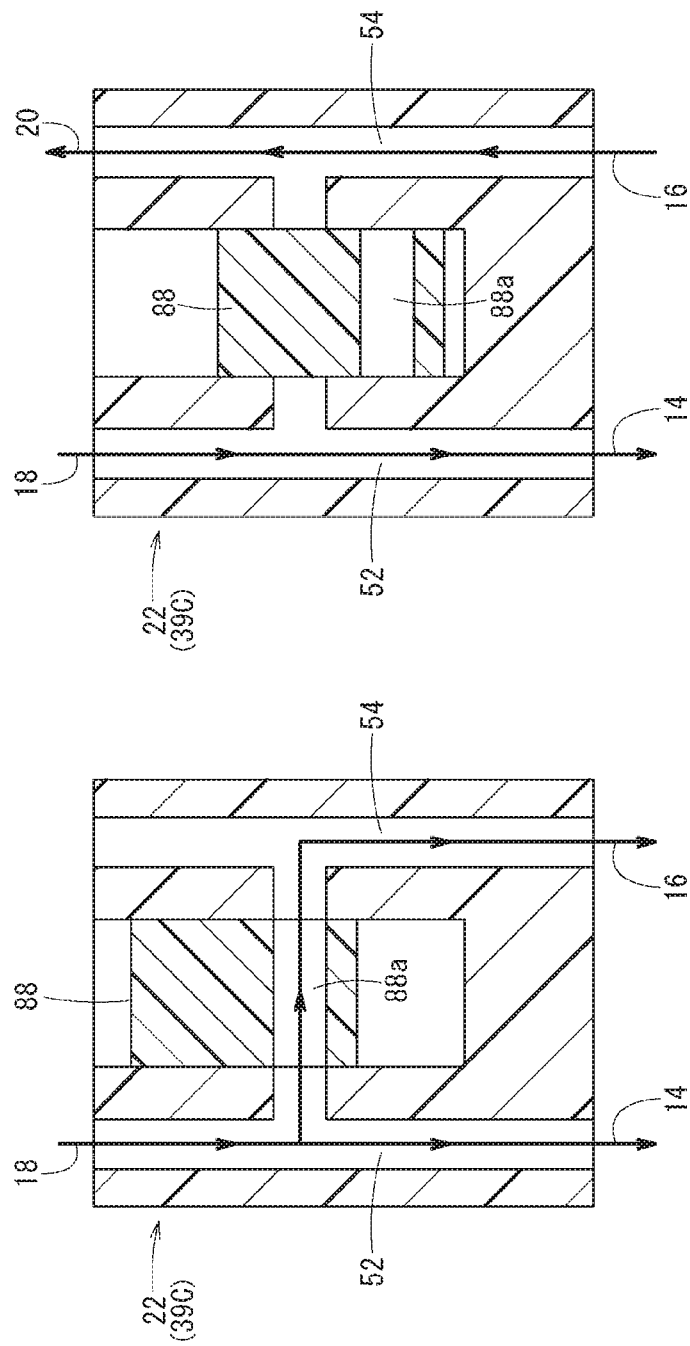

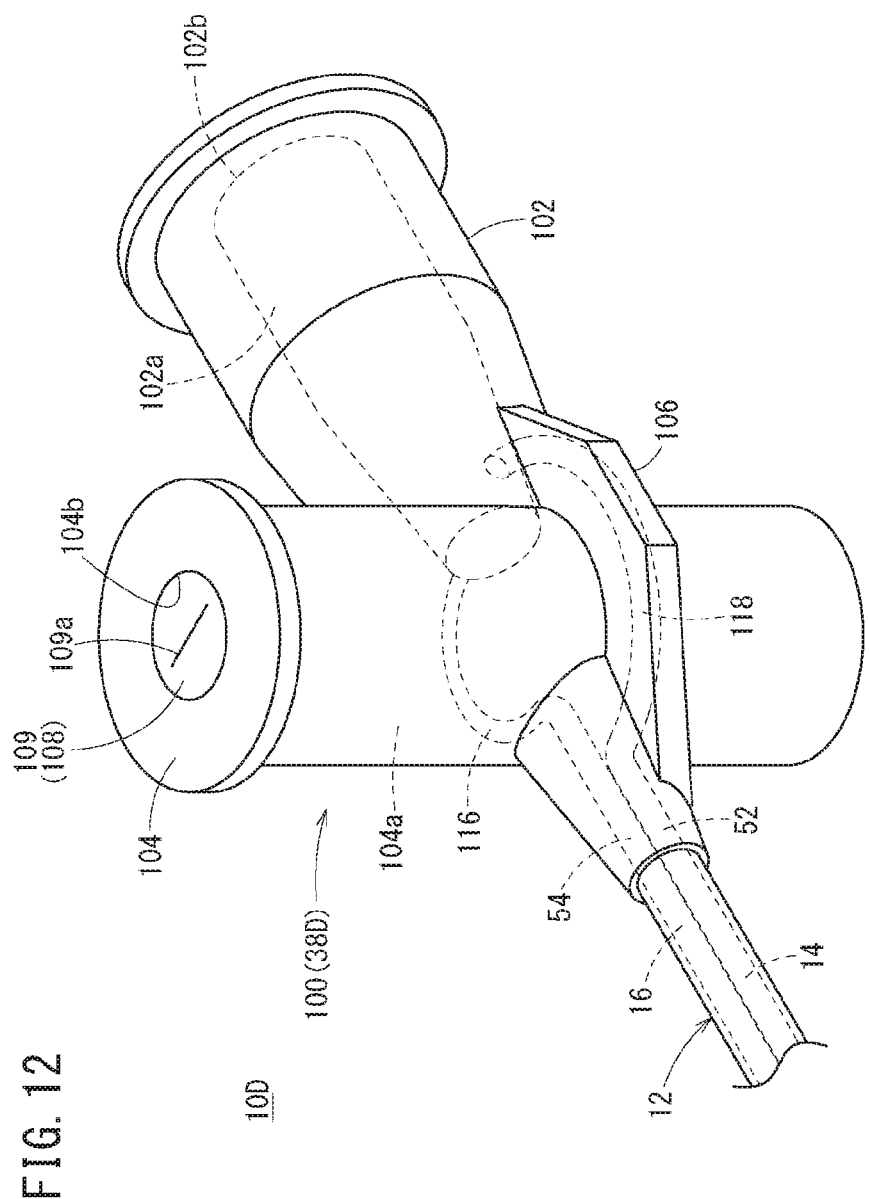

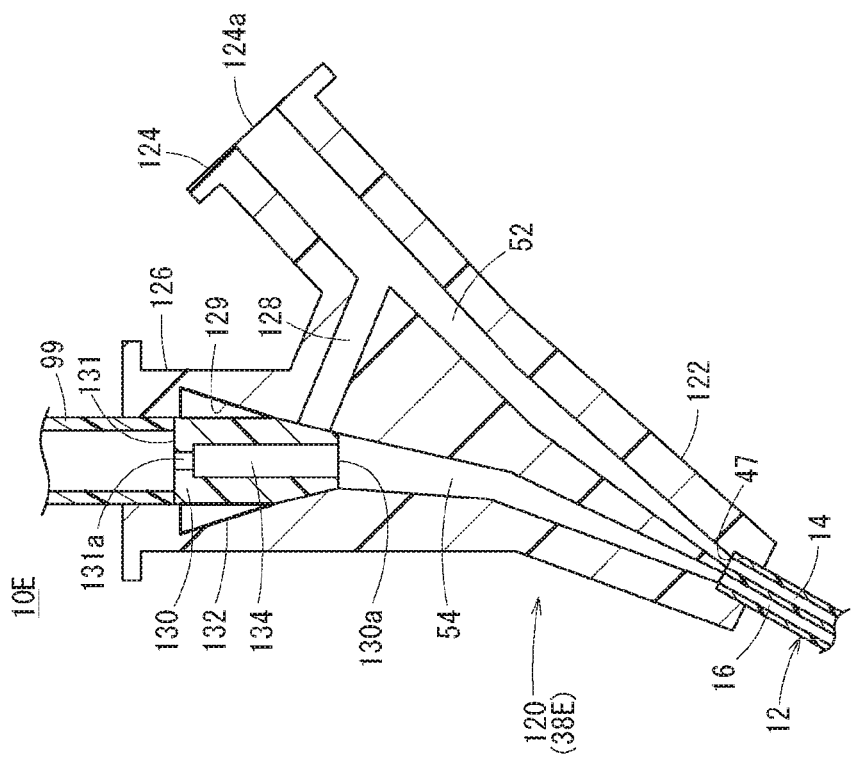
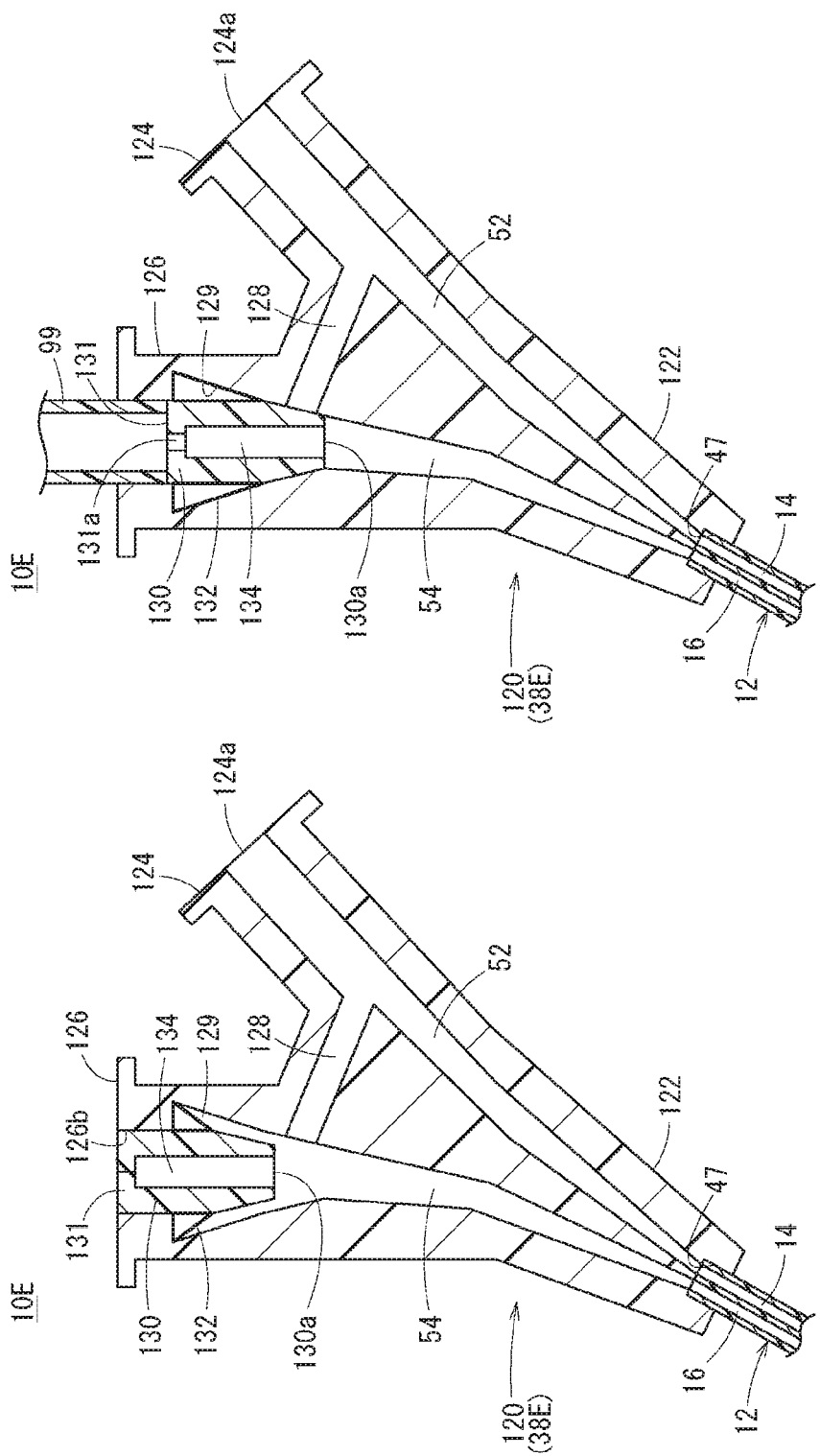

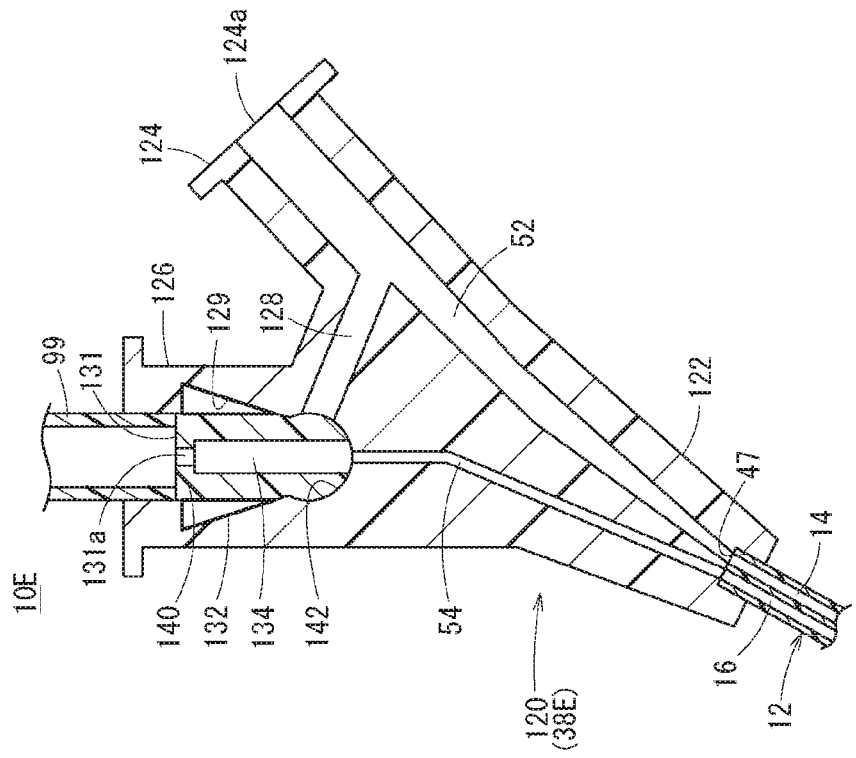
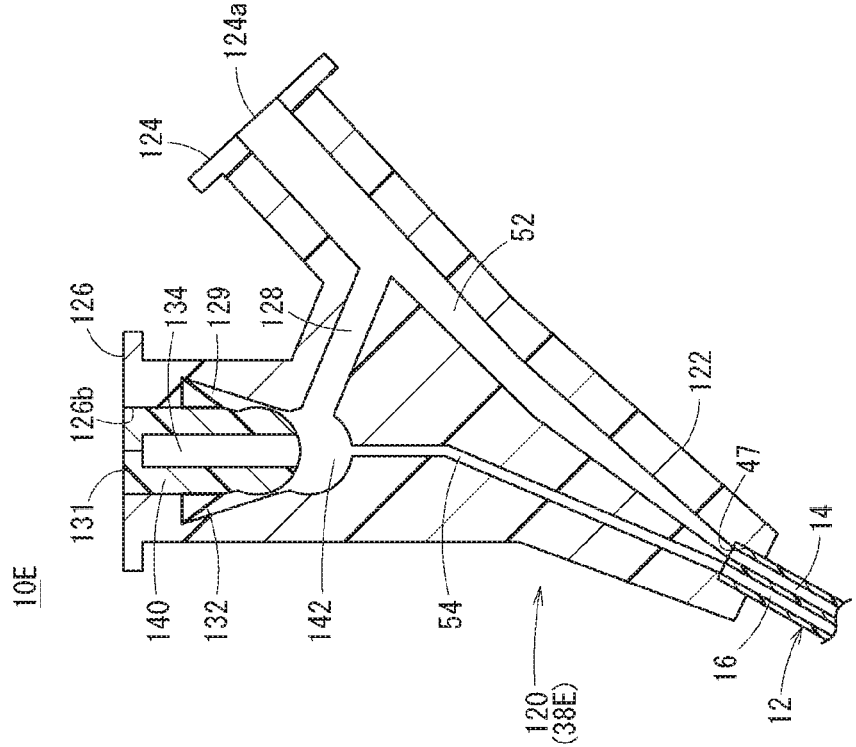

CATHETER, SWITCHING DEVICE, AND METHOD FOR OPERATING CATHETER

CROSS-REFERENCE TO RELATED APPLICATIONS

This is a bypass continuation of PCT Application No. PCT/JP2017/011393, filed on Mar. 22, 2017, which claims priority to Japanese Application No. 2016-060154, filed on Mar. 24, 2016. The contents of these applications are hereby incorporated by reference in their entireties.

BACKGROUND

The present disclosure relates to a catheter in which a liquid flows through first and second lumens, a switching device, and a method for operating the catheter.

At the time of performing an infusion on a patient, for example, a catheter having first and second lumens may be used. Blood may be sampled, central venous pressure measured, or a liquid medicine administered through the second lumen, while liquid such as a nutrient or the like may be administered though the first lumen.

In the catheter used in the infusion as described above, there is a risk that blood may coagulate due to inflow of blood into the second lumen by an influence of a pressure change, a blood pressure or the like under a condition in which the second lumen is not used. Further, when coagulation of blood occurs, coagulation of blood inhibits flow of a liquid at the time of using the second lumen. Therefore, a catheter disclosed in Japanese Patent No. 5088987 includes a one-way valve in an opening portion of the catheter communicating with a second lumen (sub lumen), thereby suppressing blood from entering the second lumen.

SUMMARY

However, in actual use, it is difficult to completely prevent blood from entering the lumen of the catheter, and the possibility of coagulation of blood that enters in the lumen still remains. Further, the catheter disclosed in Japanese Patent No. 5088987 has problems in that it may be difficult to allow a liquid to flow from an opening portion of the one-way valve, the catheter cannot be used in collecting blood, and the like.

Certain embodiments of the present disclosure have been developed in view of the above circumstances. One object of certain embodiments described herein is to provide a catheter capable of suppressing blood from entering each lumen in a catheter having a plurality of lumens by a simple configuration to allow a liquid to satisfactorily flow, to provide a switching device, and to provide a method for operating the catheter.

According to one embodiment, a catheter includes: a first port; a second port; a first lumen communicating with the first port; a second lumen communicable with the first port and the second port; and a switching mechanism part selectively switchable between a first switching state in which the first port and the second lumen communicate with each other and a second switching state in which communication between the first port and the second lumen is blocked.

In this manner, the catheter can selectively switch between the first and second switching states by the switching mechanism part, thereby making it possible to suppress blood from entering first and second lumens of the catheter. That is, in the case of using only a first port without using a second port, the catheter is in the first switching state, such that the first port and the second lumen communicate with each other, and thus, a liquid supplied to the first port can flow into the second lumen as well as the first lumen. As a result, it is possible to suppress blood from entering the second lumen, or even when blood enters the second lumen, it is possible to allow blood to flow, thereby making it possible to surely maintain communication of the second lumen. Further, in the case of using the first and second ports, the catheter is in the second switching state, such that communication between the first port and the second lumen is blocked, thereby making it possible to allow different liquids to flow into the first and second lumens, respectively.

In one aspect, the switching mechanism part blocks the second port and the second lumen in the first switching state.

As described above, the switching mechanism part can block the liquid flowing from the first port from flowing backward to the second port by blocking the second port and the second lumen in the first switching state.

Further, the switching mechanism part may be configured to have a communication path capable of communicating between the first and second lumens and switch to the second switching state by blocking or moving the communication path.

As described above, the switching mechanism part has the communication path and switches to the second switching state by blocking or moving the communication path, such that in the catheter, the first switching state in which the first and second lumens communicate with each other through the communication path and the second switching state in which communication is blocked can be simply switched.

In one aspect, the switching mechanism part includes: a body part; and a rotation part having the communication path therein and mounted to be rotatable on the body part, wherein the rotation part is configured to switch the first switching state in which the first port and the second lumen communicate with each other through the communication path and the second switching state in which the second port and the second lumen communicate with each other through the communication path by relatively rotating with respect to the body part.

As described above, the switching mechanism part includes the body part and the rotation part, such that a user of the catheter can easily switch the first switching state and the second switching state by rotating the rotation part relative to the body part.

In one aspect, the switching mechanism part may include: a tube provided between the first lumen and the second lumen and having the communication path; and a clamp that opens or closes the tube.

As described above, the switching mechanism part includes a tube having a communication path; and a clamp that opens or closes the tube, such that a user of the catheter can easily switch between the first switching state and the second switching state by opening or closing the clamp.

In one aspect, the switching mechanism part may include a valve body that opens or closes the communication path.

As described above, the switching mechanism part includes the valve body, such that the user of the catheter can easily switch between the first switching state and the second switching state by rotating the rotation part relative to the valve body.

In one aspect, the switching mechanism part includes: a body part having the communication path therein; and the valve body provided to be displaceable in the body part, wherein the valve body allows the catheter to be in the first switching state by opening the communication path in a standby state in which a connector is not inserted into the second port and allows the catheter to be in the second switching state by closing the communication path in an insertion state in which the connector is inserted into the second port.

As described above, the valve body is provided to be displaceable in the body part, and the catheter can allow a liquid to smoothly flow from the first port to the second lumen by opening the communication path in the standby state. Meanwhile, the catheter can more surely block communication between the first port and the second lumen by closing the communication path in a connection state.

Further, the switching mechanism part may be configured to include: a body part; and the valve body having the communication path and provided to be displaceable in the body part, wherein the valve body allows the catheter to be in the first switching state by opening the communication path in a standby state in which a connector is not inserted into the second port and allows the catheter to be in the second switching state by moving the communication path relative to the body part so as to close the communication path in an insertion state in which the connector is inserted into the second port.

As described above, because the communication path can be opened or closed by movement of the valve body even in the configuration in which the valve body has the communication path, the first switching state and the second switching state can be easily switched.

In one aspect, the valve body has a flow channel that allows the second port and the second lumen to communicate with each other in the insertion state.

As described above, because the valve body has the flow channel that allows the second port and the second lumen to communicate with each other, it is possible to smoothly supply a liquid from the connector of the medical instrument inserted into the second port to the flow channel, thereby making it possible to simply allow the liquid to flow to the second lumen through the flow channel.

In another embodiment, a switching device includes: a body part having a first port and a second port; a first path provided in the body part and communicating with the first port; a second path provided in the body part and communicable with the first port and second port; and a switching mechanism part selectively switchable between a first switching state in which the first port and the second path communicate with each other and a second switching state in which communication between the first port and the second path is blocked.

In this manner, the switching device can selectively switch between the first and second switching states, thereby making it possible to suppress blood from entering first and second lumens of the catheter body connected to the switching device. That is, the switching device switches to the first switching state, thereby making it possible to suppress the blood from entering the second lumen by allowing a liquid to flow to the second lumen. Further, the switching device switches to the second switching state, thereby making it possible to allow liquids to flow to the first and second lumens separately by blocking communication between the first port and the second lumen.

In another embodiment, a method for operating a catheter includes a first port; a second port; a first lumen; and a second lumen and including a switching mechanism part selectively switchable between a first switching state and a second switching state, the method including: switching the switching mechanism part to the first switching state to allow a liquid supplied from the first port to flow into the first lumen and the second lumen; and switching the switching mechanism part to the second switching state to allow the liquid supplied from the first port to flow into the first lumen and allow a liquid supplied from the second port and different from the liquid supplied from the first port to flow into the second lumen.

In a catheter, a switching device and a method for operating the catheter according to certain embodiments of the present disclosure, it is possible to suppress blood from entering each lumen of a catheter body having a plurality of lumens by a simple configuration, such that a liquid can be allowed to satisfactorily flow.

BRIEF DESCRIPTION OF THE DRAWINGS

FIG. 4A is a cross-sectional view schematically illustrating a state of the hub at the time of using only the first port, and FIG. 4B is an explanatory view illustrating an equivalent circuit of the liquid in a second switching state of the catheter.

FIG. 5A is a plan view illustrating an entire configuration of a catheter according to a second embodiment, and FIG. 5B is a partial cross-sectional view illustrating an internal structure of a connection portion between a first tube and a connection tube of FIG. 5A.

FIG. 6A is an explanatory view schematically illustrating a flow of a liquid in a first switching state of the catheter of FIG. 5A, and FIG. 6B is an explanatory view schematically illustrating a flow of the liquid in a second switching state of the catheter of FIG. 5A.

FIG. 7A is a cross-sectional view illustrating a first switching state of a switching mechanism part according to a first modified embodiment, and FIG. 7B is a cross-sectional view illustrating a second switching state of the switching mechanism part according to the first modified embodiment.

FIG. 9A is a cross-sectional view illustrating a first switching state of a switching mechanism part according to a third modified embodiment, and FIG. 9B is a cross-sectional view illustrating a second switching state of the switching mechanism part according to the third modified embodiment.

FIG. 12 is a perspective view illustrating an entire configuration of a catheter according to a fourth embodiment.

FIG. 15A is a plan cross-sectional view illustrating a first switching state of a catheter according to a fifth embodiment, and FIG. 15B is a plan cross-sectional view illustrating a second switching state of the catheter of FIG. 15A.

FIG. 16A is a plan cross-sectional view illustrating a first switching state of a catheter according to a fourth modified embodiment, and FIG. 16B is a plan cross-sectional view illustrating a second switching state of the catheter of FIG. 16A.

DETAILED DESCRIPTION

Hereinafter, a catheter, a switching device and a method for operating the catheter according to embodiments of the present disclosure are described in detail (first to fifth embodiments) with reference to the accompanying drawings.

First Embodiment

Figure 1:
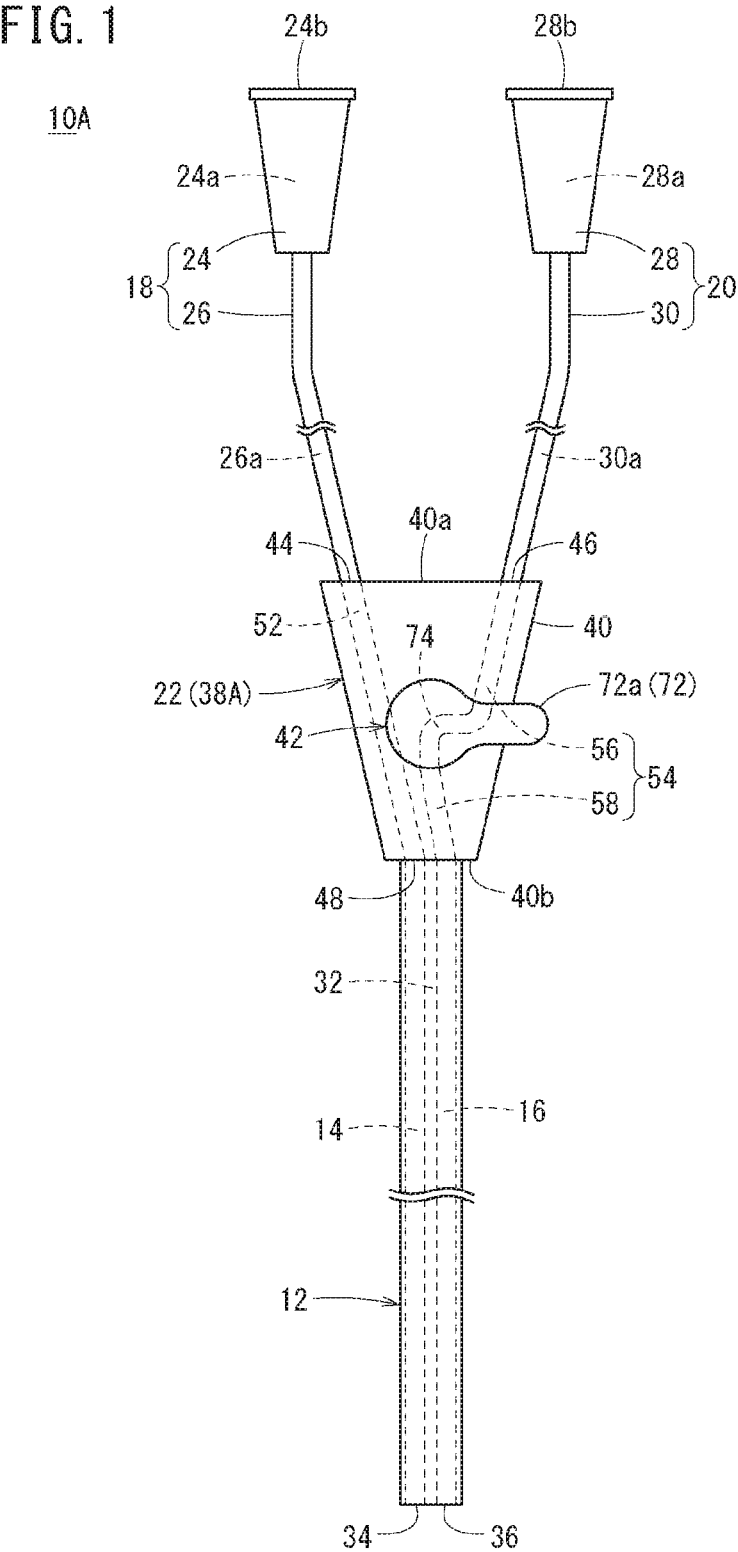
FIG. 1 is a plan view illustrating an entire configuration of a catheter according to a first embodiment.

A catheter 10A according to a first embodiment constitutes an infusion line in an infusion. That is, the catheter 10A is used as a tool connecting a medical instrument such as a medical bag or the like and a patient to each other to allow a liquid to flow. Further, as shown in FIG. 1, the catheter 10A is configured as a multi-lumen type catheter having a single catheter body 12 on a downstream portion from an intermediate position to a patient, but including a plurality of lumens in the catheter body 12. As a result, the catheter 10A has a function of collecting blood, measuring a central vein pressure, administering a liquid medicine or the like, while administering an infusion solution.

Particularly, a double lumen type catheter 10A having two lumens (a first lumen 14 and a second lumen 16) is described below (this is equally applied to second to fifth embodiments). However, catheters 10A to 10E are not limited to double lumen type catheters, but can also be appropriately modified to thereby be applied to catheters having three or more lumens.

The catheter 10A according to the first embodiment includes a first port 18, a second port 20, a hub 22, and the catheter body 12. The first and second ports 18 and 20 and the catheter body 12 are each connected to the hub 22, such that the first and second ports 18 and 20 and the catheter body 12 can be integrally handled as the single catheter 10A.

The first port 18 has a first terminal 24 to which a connector of a medical instrument (not illustrated) such as a medical bag, another catheter, a syringe or the like is connected at the time of infusion; and a first tube 26 having a first end connected to the first terminal 24 and a second end connected to the hub 22. The first terminal 24 and the first tube 26, and the first tube 26 and the hub 22 are firmly fixed to each other by an appropriate fixing method such as vibration fusion, high-frequency fusion, welding, adhesion or the like.

The first terminal 24 is relatively hard and is formed in a shape of a cylinder having a first hollow part 24a. The first tube 26 is connected to the first end (downstream end) thereof. A first terminal hole 24b communicating with the first hollow part 24a is provided at an end portion of the first terminal 24 on the side opposite to the first tube 26.

The first tube 26 has a first conduction path 26a therein and is formed of a tube body having a predetermined length. The first conduction path 26a penetrates in the first tube 26 in an axial direction and communicates with the first hollow part 24a of the first terminal 24. Therefore, the first hollow part 24a and the first conduction path 26a allow the liquid such as the infusion solution or the like to flow from the medical instrument connected to the first terminal 24 to the hub 22 on the downstream side.

The first tube 26 is made of a material more flexible than that of the first terminal 24, thereby securing flexibility in a disposition state of the first port 18 on the upstream side of the hub 22. The material constituting the first tube 26 is not particularly limited, but examples of the material may include polyolefin based resins such as high-density polyethylene, polypropylene, polybutene, vinyl chloride, an ethylene-vinyl acetate copolymer and the like or polyolefine based elastomers thereof, fluorine based resins or fluorine based elastomers, methacrylic resins, polyphenylene oxide, modified polyphenylene ether, polyethylene terephthalate, polybutylene terephthalate, polyether ether ketone, polyamideimide, polyetherimide, polyether sulfone, cyclic polyolefins, polyurethane based elastomers, polyester based elastomers, polyamide or polyamide based elastomers, polycarbonate, polyacetal, styrene based resins or styrene based elastomers, thermoplastic polyimide and the like.

Similarly, the second port 20 has a second terminal 28 to which a medical instrument (not illustrated) (a medical instrument different from the medical instrument connected to the first port 18) such as a medical bag, another catheter, a syringe or the like is connected; and a second tube 30 having a first end connected to the second terminal 28 and a second end connected to the hub 22. The second terminal 28 includes a second hollow part 28a therein and a second terminal hole 28b communicating with the second hollow part 28a in an end portion on the side opposite to the second tube 30. The first and second terminals 24 and 28 may be formed in the same shape, or may be formed in different shapes from each other in order to be connected to different medical instruments.

The second tube 30 has a second conduction path 30a therein and is formed of a tube body having a length approximately equal to that of the first tube 26. The second conduction path 30a penetrates in the second tube 30 in the axial direction and communicates with the second hollow part 28a of the second terminal 28. A material constituting the second tube 30 is not particularly limited, but the materials exemplified in the first tube 26 may be applied. The first and second tubes 26 and 30 may have different lengths from each other.

Further, the catheter 10A is not limited to the configuration of the first and second ports 18 and 20, but for example, the catheter 10A may have a configuration in which one or both of the first and second terminals 24 and 28 are connected to the hub 22 and the tube is omitted. On the contrary, at least one of the first and second ports 18 and 20 may not include a terminal, and the first or second tube 26, 30 may be directly connected to the medical instrument. Further, the catheter 10A may have a configuration in which the catheter 10A does not include at least one of the first and second ports 18 and 20, but the hub 22 is directly connected to another medical instrument. In this case, a connection part between the hub 22 and another medical instrument corresponds to the first or second port 18, 20.

Meanwhile, the catheter body 12 of the catheter 10A is connected to an end portion of the hub 22 on the side opposite to the end portion of the hub 22 connected to the first and second ports 18 and 20. The catheter body 12 is configured as a relatively long tube body (for example, longer than the first or second tube 26, 30).

An upstream end portion of the catheter 12 is inserted into the hub 22, and fixed thereto by an appropriate fixing method such as vibration fusion, high-frequency fusion, welding, adhesion or the like. A downstream end portion of the catheter body 12 is connected to an indwelling needle (not illustrated) constructing a liquid inflow and outflow part on the body surface of a patient. In addition, the downstream end portion of the catheter body 12 of the catheter 10A itself may be inserted into the body of the patient.

Further, as described above, the first and second lumens 14 and 16 extended in the axial direction are provided in the catheter body 12. An upstream side of the first lumen 14 communicates with a first path 52 of the hub 22. An upstream side of the second lumen 16 communicates with a second path 54 of the hub 22.

The first and second lumens 14 and 16 are separated from each other by a partition wall 32 formed in the catheter 12. The partition wall 32 extends from an upstream end to a downstream end of the catheter 12 in the axial direction. Therefore, the lower end of the catheter body 12 is provided with a first catheter hole 34 communicating with the first lumen 14 and a second catheter hole 36 communicating with the second lumen 16. In addition, a hole part through which the liquid of the catheter body 12 flows in or out may be freely designed. For example, the second catheter hole 36 may be provided on a side surface of the catheter body 12.

Further, the first and second lumens 14 and 16 are separated from each other by the partition wall 32, such that, in a cross-section view of the catheter 12 orthogonal to the axial direction, the first and second lumens 14 and 16 are each formed in a semicircular shape, and extended in parallel with each other in the axial direction of the catheter body 12. The cross-sectional shapes of the first and second lumens 14 and 16 are not limited to the semicircular shape, but rather the first and second lumens 14 and 16 may be formed in a circular shape, an oval shape, a polygonal shape, or the like. Alternatively, one of the first and second lumens 14 and 16 may be formed in a circular shape and the other may be formed in an arc shape partially enclosing the circular shape.

Flow channel cross-sectional areas of the first and second lumens 14 and 16 (or respective perimeters of the first and second lumens 14 and 16) are set to be equal to each other. However, the flow channel cross-sectional areas of the first and second lumens 14 and 16 may be different from each other. For example, the first lumen 14 may have a larger flow channel cross-sectional area than that of the second lumen 16, such that the first lumen 14 defines a main lumen through which a main infusion solution such as a nutrient or the like is administered, and the second lumen 16 defines a sub lumen through which an infusion solution such as another liquid medicine or the like is administered in advance in the catheter 10A. That is, a ratio of the flow channel cross-sectional areas of the first and second lumens 14 and 16 may be set depending on the use.

Dimensions of the catheter body 12 are not particularly limited, but for example, the catheter body 12 may have an overall length of about 200 mm to 2000 mm and an outer diameter of about 1 mm to 10 mm. A material constituting the catheter 12 is not particularly limited, but for example, the materials described for the first tube 26 may be applied.

The hub 22 is a member for intermediating between the first and second ports 18 and 20 on the upstream side and the catheter body 12 on the downstream side. The hub 22 allows a liquid flowing from the first and second ports 18 and 20 to flow to the first and second lumens 14 and 16 of the catheter body 12. Further, the hub 22 allows a liquid flowing from the first or second lumen 14, 16 to flow to the first or second port 18, 20 in the case of collecting blood from a patient. Particularly, the hub 22 according to the first embodiment is configured as a switching mechanism part 38A (switching device) that switches communication of the first and second ports 18 and 20 with the first and second lumens 14 and 16.

In detail, the switching mechanism part 38A has a block body 40 (body part); and a cock 42 (rotation part) mounted to be rotatable on the block body 40.

Figure 2:
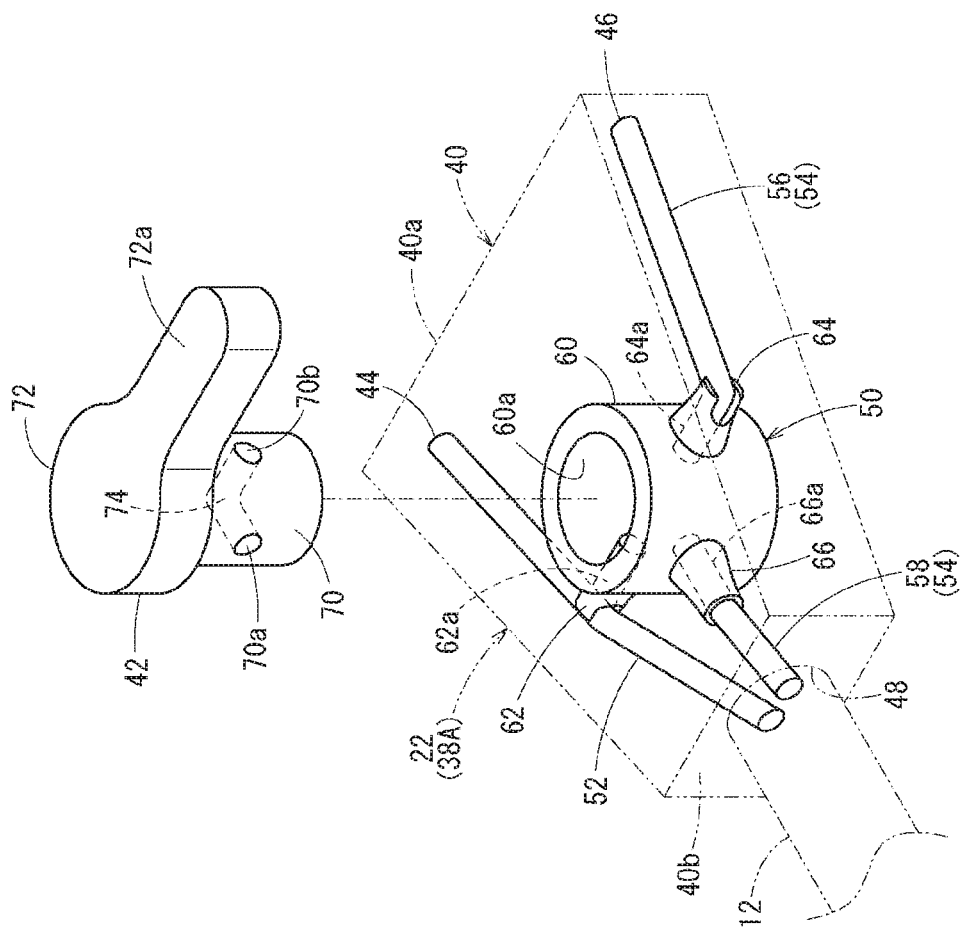
FIG. 2 is an enlarged perspective view illustrating a hub of the catheter of FIG. 1.

The block body 40 is formed to be harder than the catheter body 12 and the first and second tubes 26 and 30. In a plan view, the block body 40 has a trapezoidal shape of which an upper base side (upper base surface 40a) is long and a lower base side (lower base surface 40b) is shorter than the upper base surface 40a. Further, as illustrated in FIG. 2, the block body 40 has a predetermined thickness in order to form a liquid path therein.

The upper base surface 40a of the block body 40 is simultaneously provided with a first insertion hole 44 into which the first port 18 is inserted and a second insertion hole 46 into which the second port 20 is inserted. The lower base surface 40b of the block body 40 is provided with a third insertion hole 48 into which the catheter body 12 is inserted. Further, in the plan view, the block body 40 includes a mounting tube 50 in an intermediate portion between the upper base surface 40a and the lower base surface 40b and a central portion in a width direction.

Further, the block body 40 has a first path 52 that allows the first and third insertion holes 44 and 48 to communicate with each other; and a second path 54 that allows the second and third insertion holes 46 and 48 to communicate with each other.

The first path 52 has an inner diameter equal to (or slightly smaller than) an outer diameter of the first tube 26, such that the first tube 26 can be inserted thereinto. The first path 52 fixes the first port 18 inserted into the first insertion hole 44 to communicate with the first conduction path 26a, and communicates with the first lumen 14 of the catheter body 12 inserted into the third insertion hole 48. A predetermined range of the block body 40 in the vicinity of the third insertion hole 48, which is a mounting hole 47 for inserting and fixing the catheter body 12, is formed to have an inner diameter larger than that of the first or second path 52, 54 (see FIG. 3A).

On the other hand, the second path 54 is divided into two paths (a second upstream path 56 and a second downstream path 58) with the mounting tube 50 interposed therebetween. The second upstream path 56 is provided in a range from the second insertion hole 46 to the mounting tube 50, and the second downstream path 58 is provided in a range from the mounting tube 50 to the inside of the mounting hole 47.

The second upstream path 56 has an inner diameter equal to (or slightly smaller than) an outer diameter of the second tube 30, such that the second tube 30 can be inserted thereinto. The second upstream path 56 fixes the second port 20 inserted into the second insertion hole 46 to communicate with the second conduction path 30a. The second downstream path 58 is formed to have the same diameter as that of the second upstream path 56 and communicates with the second lumen 16 of the catheter body 12 inserted into the mounting hole 47.

Meanwhile, the mounting tube 50 of the block body 40 is provided for rotatably mounting the cock 42. For example, the block body 40 is insert-molded in a pre-formed mounting tube 50, thereby covering the outside of the mounting tube 50 to constitute an exterior of the hub 22. The mounting tube 50 includes a tube part 60 having a cavity 60a into which the cock 42 is inserted; and three protrusion nozzles (a first protrusion nozzle 62, a second protrusion nozzle 64 and a third protrusion nozzle 66) provided on an outer peripheral surface of the tube part 60.

The tube part 60 is formed in a cylindrical shape in which the cavity 60a penetrates the tube part 60 or the tube part has a bottom part closing the cavity 60a on one side (opposite to an insertion side of the cock 42), and the tube part 60 is disposed to penetrate the block body 40 in a thickness direction. It is preferable that a locking mechanism (for example, a structure in which convex and concave parts engage each other in a circumferential direction) preventing detachment of the cock 42 in cooperation with an outer peripheral surface of the cock 42 inserted into the cavity 60a is provided on inner peripheral surface of the tube part 60 constituting the cavity 60a.

Each of the protrusion nozzles 62, 64 and 66 is provided at the same height in the thickness direction of the block body 40 and installed on an outer peripheral surface of the tube part 60 to be deviated from each other by 90° in the circumferential direction. The protrusion nozzles 62, 64 and 66 are formed in a conical shape that tapers toward protrusion end portions, respectively, and nozzle holes 62a, 64a and 66a penetrating axial centers thereof to communicate with the cavity 60a are provided therein, respectively. In addition, the first protrusion nozzle 62 communicates with the first path 52, the second protrusion nozzle 64 communicates with the second upstream path 56, and the third protrusion nozzle 66 communicates with the second downstream path 58.

The first protrusion nozzle 62 is configured to come in contact with a lateral side of the first path 52, and allows the nozzle hole 62a to communicate with the first path 52. A protrusion end portion of the first protrusion nozzle 62 has an end surface depressed in a letter U shape, such that the first path 52 is inserted thereinto in the thickness direction. In this way, the first protrusion nozzle 62 allows the nozzle hole 62a to be communication with the lateral side without blocking the extension of the first path 52.

The second protrusion nozzle 64 is also configured to come in contact with a lateral side of the second upstream path 56, and allows the nozzle hole 64a to communicate with the second upstream path 56. A protrusion end portion of the second protrusion nozzle 64 is depressed in a letter U shape, similarly to the first protrusion nozzle 62, such that the second upstream path 56 is inserted thereinto in the thickness direction. Further, the hub 22 liquid-tightly closes an inner end portion of the second upstream path 56 by providing a filler 68 (see FIG. 3A) made of a resin material in the second upstream path 56 inside the second protrusion nozzle 64. Therefore, the second upstream path 56 communicates with the nozzle hole 64a of the second protrusion nozzle 64 while communicating with the second insertion hole 46 of the upper base surface 40a, thereby allowing the liquids to flow entirely in the nozzle hole 64a.

The third protrusion nozzle 66 is configured to face the second downstream path 58 at a protrusion end portion thereof, and allows an end portion of the second downstream path 58 and the nozzle hole 66a to be communication with each other. That is, the second path 54 can communicate with the second upstream path 56 and the second downstream path 58 through the mounting tube 50. Meanwhile, the second downstream path 58 can also communicate with the first path 52 depending on a rotational position of the cock 42. At this time, the second path 54 is in a blocked state.

The cock 42 has a cylindrical inserted part 70 to be inserted into the cavity 60a of the mounting tube 50; and an operation part 72 connected to a first end portion of the inserted part 70 and exposed to a surface of the block body 40. The inserted part 70 is formed to have an outer diameter substantially equal to an inner diameter of the inner peripheral surface constituting the cavity 60a of the mounting tube 50. Therefore, in a state in which the inserted part 70 is inserted into the cavity 60a, the inserted part 70 can be relatively slidable in the circumferential direction of the cavity 60a while liquid-tightly closing the cavity 60a.

A communication path 74 allowing the liquid to flow is formed in the inserted part 70. In a cross-section orthogonal to an axial line of the inserted part 70, the communication path 74 is formed in a letter L shape, and communicates a first opening 70a and a second opening 70b provided at positions deviated from each other by 90° on an outer peripheral surface of the inserted part 70. In the state in which the inserted part 70 is inserted into the cavity 60a, the first and second openings 70a and 70b are disposed at the same height as the nozzle holes 62a, 64a and 66a of the respective protrusion nozzles 62, 64 and 66, thereby making it possible to allow the communication path 74 and the respective nozzle holes 62a, 64a and 66a to communicate with each other.

Figure 3B:
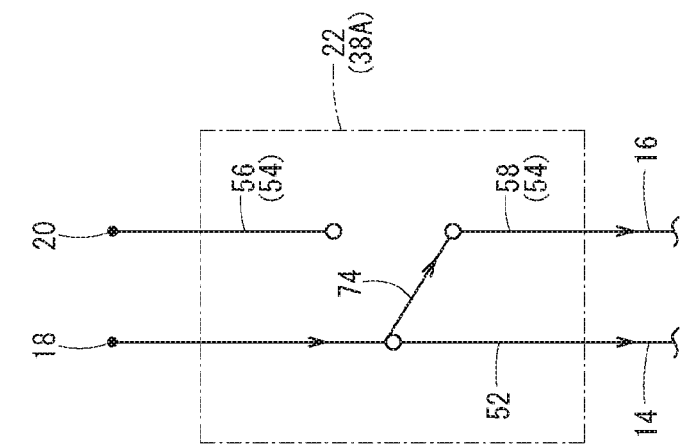
FIG. 3B is an explanatory view illustrating an equivalent circuit of a liquid in a first switching state of the catheter.
Figure 3A:
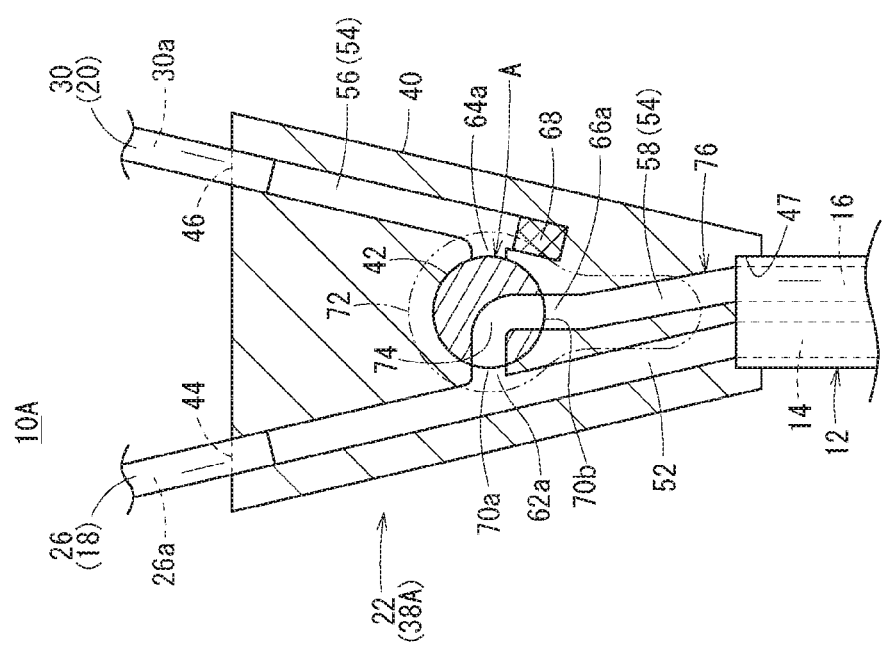
FIG. 3A is a cross-sectional view schematically illustrating a state of the hub at the time of using first and second ports.

In detail, as illustrated in FIG. 3A, the cock 42 is positioned at a first rotational position A at which the first opening 70a faces the nozzle hole 62a of the first protrusion nozzle 62 and the second opening 70b faces the nozzle hole 66a of the third protrusion nozzle 66, such that the cock 42 is in a first switching state in which the communication path 74 allows the first path 52 and the second downstream path 58 to communicate with each other. Meanwhile, as illustrated in FIG. 4A, the cock 42 is positioned at a second rotational position B at which the second opening 70b faces the nozzle hole 64a of the second protrusion nozzle 64 and the first opening 70a faces the nozzle hole 66a of the third protrusion nozzle 66, such that the cock 42 is in a second switching state in which the communication path 74 allows the second upstream path 56 and the second downstream path 58 to communicate with each other. That is, the cock 42 switches a target to communicate with the communication path 74 by rotational movement between the first rotational position A and the second rotational position B.

Further, the operation part 72 has a knob 72a protruding from a side peripheral surface of a disc-like part connected to the inserted portion 70 toward the outside by a predetermined length. A position where the second opening 70b is provided on the outer peripheral surface of the inserted part 70 and a position in the circumferential direction where the knob 72a of the operation part 72 is provided overlap each other. Therefore, a user can confirm the position of the knob 72a to recognize whether the catheter is in the first switching state or the second switching state.

Further, the block body 40 and the cock 42 may have a latch mechanism allowing the block body 40 and the cock 42 to engage with each other with a light engagement force at the first rotational position A and the second rotational position B. For example, the latch mechanism may be constituted by a protrusion provided on the outer peripheral surface of the inserted part 70 and a depressed part of the inner circumferential surface of the mounting tube 50 into which the protrusion is inserted.

The catheter 10A according to the first embodiment is basically configured as described above, and functions and effects thereof are described below.

The catheter 10A is applied to an infusion line, and the downstream end portion of the catheter body 12 is placed in the blood vessel of a patient. In addition, for example, the catheter 10A can be in a first use state in which a medical bag (medical instrument) containing a nutrient (liquid) is connected to the first port 18 and the second port 20 is not used. Further, for example, the catheter 10A can be in a second use state in which the medical bag containing the nutrient is connected to the first port 18 and another medical bag (another medical instrument) containing a liquid medicine (liquid) is connected to the second port 20.

First, the first use state of the catheter 10A is described with reference to FIGS. 3A and 3B. In this first use state, a user such as a doctor, a nurse or the like rotates the cock 42 relative to the block body 40 to dispose the cock 42 at the first rotational position A (in the first switching state). As described above, in this state, the first opening 70a of the cock 42 faces the first path 52, and the second opening 70b faces the second downstream path 58. Further, the cock 42 is positioned at the first rotational position A, such that the outer peripheral surface of the cock 42 closes the nozzle hole 64a of the second protrusion nozzle 64 to block communication of the second upstream path 56 of the hub 22.

Therefore, in the first switching state, a path constituted by the first path 52 and a path (referred to as a branch path 76) in which the nozzle hole 62a of the first protrusion nozzle 62, the communication path 74, the nozzle hole 66a of the third protrusion nozzle 66 and the second downstream path 58 communicate with each other are formed. Therefore, the liquid supplied from the first port 18 is divided into a liquid introduced into the first lumen 14 through the first path 52 and a liquid introduced into the second lumen 16 through the branch path 76.

Accordingly, the liquid supplied from the first port 18 stably flows toward an upstream side of the first path 52 and a portion of the liquid passes through the first path 52 to flow toward the first lumen 14 communicating with the downstream of the first path 52. Further, the other portion of the liquid introduced into the nozzle hole 62a and passes through the branch path 76 to flow to the second lumen 16 communicating with the downstream of the second downstream path 58.

As described above, in a conventional catheter, there is a risk that when a second port and a second lumen are not used and a liquid does not flow, blood will be introduced into the second lumen for reasons such as a pressure change or the like. Further, when the blood is introduced into the second lumen as described above, coagulation occurs, thereby causing a cause of hindering flow when the liquid flows through the second lumen in some cases. On the contrary, in the catheter 10A according to the present embodiment, when the second port 20 is not used, the liquid flowing in the first path 52 is divided and also flows even in the branch path 76 (the second downstream path 58). In this way, because the liquid flows in the second lumen 16, it is possible to suppress the blood from entering the second lumen 16, and even in the case in which the blood enters the second lumen 16, the blood can be pushed out by the liquid.

Next, as illustrated in FIGS. 4A and 4B, the second use state of the catheter 10A is described. In this second use state, the user such as the doctor, the nurse or the like rotates the cock 42 relative to the block body 40 to dispose the cock 42 at the second rotational position B (in the second switching state). As described above, in this state, the first opening 70a of the cock 42 faces the second downstream path 58, and the second opening 70b faces the second upstream path 56. Therefore, a path (because the second upstream path 56 and the second downstream path 58 communicates with each other, for convenience of explanation, this path is referred to as the second path 54) in which the second upstream path 56, the nozzle hole 64a of the second protrusion nozzle 64, the communication path 74, the nozzle hole 66a of the third protrusion nozzle 66 and the second downstream path 58 communicate with each other is formed. Therefore, the liquid supplied from the second port 20 is introduced into the second lumen 16 facing the second downstream path 58 through the second path 54.

Meanwhile, the cock 42 is positioned at the second rotational position B, such that the outer peripheral surface of the cock 42 closes the nozzle hole 62a of the first protrusion nozzle 62 to block communication of the first path 52 of the hub 22. Therefore, introduction of the liquid supplied from the first port 18 into the nozzle hole 62a is prevented, and the liquid supplied from the first port 18 is introduced into the first lumen 14 facing the first path 52 through the first path 52.

In this way, the liquid supplied from the first port 18 stably flows in the first path 52, and the liquid supplied from the second port 20 stably flows in the second path 54. As a result, the liquid flowing in the first path 52 does not enter the second path 54 but is introduced into the first lumen 14 to thereby be administered to a patient through the first lumen 14. Further, the liquid flowing in the second path 54 also does not enter the first path 52 but is introduced into the second lumen 16 to thereby be administered to the patient through the second lumen 16.

That is, in the case of illustrating an equivalent circuit for flowing the liquid (see FIGS. 3B and 4B), in the catheter 10A, the switching mechanism part 38A in which the communication path 74 constituting a switching portion is selectively switched to the first path 52 or the second upstream path 56 is configured. Therefore, in both a pattern for supplying the liquid from only the first port 18 and a pattern for supplying liquids from the first and second ports 18 and 20, respectively, it is possible to allow the liquid to normally flow to the first and second lumens 14 and 16.

As described above, in the catheter 10A according to the first embodiment, the first and second switching states can be selectively switched by the hub 22, thereby making it possible to suppress the blood from entering the first and second lumens 14 and 16. That is, in the case in which the second port 20 is not used and only the first port 18 is used, the catheter 10A is in the first switching state, such that the first port 18 and the second lumen 16 communicate with each other, thereby allowing the liquid supplied to the first port 18 to flow to the second lumen 16. As a result, it is possible to suppress the blood from entering the second lumen 16, or even when the blood enters the second lumen 16, it is possible to allow the blood to flow, thereby making it possible to surely maintain a communication state of the second lumen 16. Further, in the case of using the first and second ports 18 and 20, the catheter 10A is in the second switching state to block communication between the first port 18 and the second lumen 16, such that the liquids can be allowed to flow separately to the first and second lumens 14 and 16.

In this case, the hub 22 blocks the second port 20 and the second lumen 16 from each other in the first switching state, thereby making it possible to prevent backflow of the liquid flowed from the first port 18 from flowing backward to the second port 20.

The hub 22 is configured to have the communication path 74 and move the communication path 74, whereby in the catheter 10A, the first switching state in which the first and second lumens 14 and 16 communicate with each other through the communication path 74 and the second switching state in which the communication is blocked can be simply switched. Further, the hub 22 is configured to include the block body 40 and the cock 42, such that the user of the catheter 10A can easily switch the first and second switching states to each other by rotating the cock 42 having a communication path 74 relative to the block body 40.

In addition, the catheter 10A is not limited to the above-mentioned configuration, but can be variously modified and applied. For example, the hub 22 may be provided as a switching device formed of a single body without the first terminal 24, the first tube 26, the second terminal 28, the second tube 30 and the catheter body 12. In this case, two catheters, a connector of a medical bag, a syringe or the like is connected to an upstream side of the hub 22 and a catheter body 12 is simultaneously connected to a downstream side of the hub 22 in a medical site, such that the hub 22 (switching device) may exhibit the same function.

Hereinafter, catheters according to other embodiments (second to fifth embodiments) of the present disclosure are described. Further, in the following description, the components having the same configurations or the same functions as those of the catheter 10A according to the first embodiment are denoted by the same reference numerals, and a description thereof is omitted.

Second Embodiment

A catheter 10B according to the second embodiment is different from the catheter 10A according to the first embodiment in that a connection tube 80 and a clamp 82 are provided as a switching mechanism part 38B between first and second tubes 26 and 30 as illustrated in FIG. 5A.

In this case, a first port 18 of the catheter 10B has a first terminal 24 and the first tube 26, and the connection tube 80 is connected to the first tube 26 at an intermediate position in an extension direction. Further, a second port 20 of the catheter 10B has a second terminal 28 and the second tube 30, and the connection tube 80 is connected to the second tube 30 at an intermediate position in an extension direction. In addition, a check valve 84 may be provided in a second hollow part 28a of the second terminal 28 in order to prevent a back flow of blood.

Meanwhile, a hub 22 constituting a portion of the switching mechanism part 38B is provided in a downstream side (downstream end portions of the first and second tubes 26 and 30) rather than the connection tube 80. The hub 22 includes first and second paths 52 and 54 independently of each other (so as not to communicate with each other). Therefore, in a state in which the first tube 26, the second tube 30 and a catheter body 12 are respectively connected to the hub 22, a first conduction path 26a, the first path 52 and a first lumen 14 communicate with each other, and at the same time, a second conduction path 30a, the second path 54 and a second lumen 16 communicate with each other.

The connection tube 80 has a communication path 80a communicating with the first and second conduction paths 26a and 30a therein. In other words, it may be said that the communication path 80a communicates with the first and second lumens 14 and 16 through the paths (the first and second paths 52 and 54) of the hub 22. In a connection portion between the first tube 26 (or the second tube 30) and the connection tube 80, tube parts of a T-shaped joint 86 are inserted into the first conduction path 26a (or the second conduction path 30a) and the communication path 80a, respectively, such that the first tube 26 and the connection tube 80 are firmly connected to each other.

The clamp 82 is mounted on an outer peripheral surface of the connection tube 80 and can be switched to an open state and a closed state by an operation of a user. Further, in the open state of the clamp 82, the communication path 80a is opened, thereby communicating the first and second conduction paths 26a and 30a with each other. In this state, a first switching state in which the first port 18 and the second lumen 16 communicate with each other through the communication path 74 is established. Meanwhile, in the closed state of the clamp 82, the communication path 80a is closed, thereby blocking communication between the first and second conduction paths 26a and 30a. In this state, a second switching state in which communications between the first port 18 and the second lumen 16 is blocked is established. Further, a configuration for opening and closing the communication path 80a is not limited to the clamp 82, but various members having an opening and closing function can be applied.

The catheter 10B according to the second embodiment is basically configured as described above, and functions and effects of the catheter 10B are described below.

It is possible to selectively select the first and second switching states of the catheter 10B similarly to the catheter 10A according to the first embodiment. For example, in the case in which a liquid is administered from only the first port 18 and the second port 20 is not used, a user switches the catheter 10B to the first switching state as illustrated in FIG. 6A.

In the first switching state, the first port 18 and the second lumen 16 are in a communication state by opening the clamp 82. That is, the first port 18 communicates with the first lumen 14 of the catheter body 12 through the first conduction path 26a and the first path 52, such that a portion of the liquid is allowed to flow from the medical instrument connected to the first port 18. Further, the first port 18 communicates with the second lumen 16 through an upstream portion of the first conduction path 26a, the communication path 80a, a downstream portion of the second conduction path 30a and the second path 54, such that a portion of the liquid from the first port 18 is allowed to flow.

Therefore, in the catheter 10B, even in the case in which the second port 20 is not used, the liquid is allowed to flow from the first port 18 to the second lumen 16. As a result, the catheter 10B can suppress an inconvenience such as introduction of blood into the second lumen 16, coagulation of the introduced blood, or the like. Further, the second terminal 28 of the second port 20 accommodates the check valve 84, thereby preventing the liquid flowing to the second conduction path 30a from being discharged from the second port 20 via the communication path 74. Further, in the catheter 10B, even in the case in which the first port 18 is not used, and the liquid is administered from only the second port 20, it is possible to allow the liquid of the second port 20 to flow to the first lumen 14 through the communication path 80a, such that blockage of the first lumen 14 can be suppressed.

Meanwhile, in the case of administering different liquids through the first and second lumens 14 and 16, the case of collecting blood through the second lumen 16 while administering the liquid through the first lumen 14 or the like, the catheter 10B is switched to the second switching state as illustrated in FIG. 6B. Further, a flow of the liquid at the time of collecting the blood through the second lumen 16 is indicated by an arrow in FIG. 6B.

In the second switching state, the communication state of the first port 18 and the second lumen 16 is blocked by closing the clamp 82 to block the communication path 80a. That is, the first port 18 communicates with only the first lumen 14 through the first conduction path 26a and the first path 52 to allow the liquid to flow. Further, the second port 20 communicates with only the second lumen 16 through the second conduction path 30a and the second path 54 to impart a suction force (negative pressure) from the second port 20, thereby allowing blood of a patient to flow toward another medical instrument (syringe or the like) connected to the second port 20.

As described above, the catheter 10B according to the second embodiment can also obtain the same effects as those of the catheter 10A. Particularly, in this catheter 10B, the switching mechanism part 38B is configured to include the connection tube 80 having the communication path 80a; and the clamp 82 that opens or closes the connection tube 80. Therefore, the user of the catheter 10B can easily switch between the first switching state and the second switching state merely by operating the opening and closing of the clamp 82 exposed on the upstream side of the hub 22.

A switching mechanism part 39A according to a first modified embodiment illustrated in FIGS. 7A and 7B is different from the switching mechanism parts 38A and 38B in that instead of the connection tube 80 and the clamp 82, communication or non-communication of a communication path 77 between first and second paths 52 and 54 provided in a hub 22 is switched. This switching mechanism part 39A has an opening and closing member 78 that enters or retreats from the hub 22. The opening and closing member 78 is configured, for example, as a spindle having a screw part 78a inserted into the hub 22 and a handle 78b connected to a first end of the screw part 78a and exposed to the hub 22.

In this case, the switching mechanism part 39A allows the communication path 77 to be in a first switching state at a position at which the opening and closing member 78 retreats outward from the hub 22. Therefore, the switching mechanism part 39A can allow a liquid in the first path 52 (first port 18) to flow even toward the second lumen 16, thereby making it possible to suppress the blood from being introduced into the second lumen 16.

When a user rotates the handle 78b in a predetermined direction in the first switching state to allow the opening and closing member 78 to advance toward the inside of the hub 22, the screw part 78a closes the communication path 77. Therefore, the switching mechanism part 39A blocks communication between the first and second paths 52 and 54, such that the liquid of the first port 18 can be allowed to flow to only the first lumen 14, and the liquid of the second port 20 can be allowed to flow to only the second lumen 16.

Figure 8A:
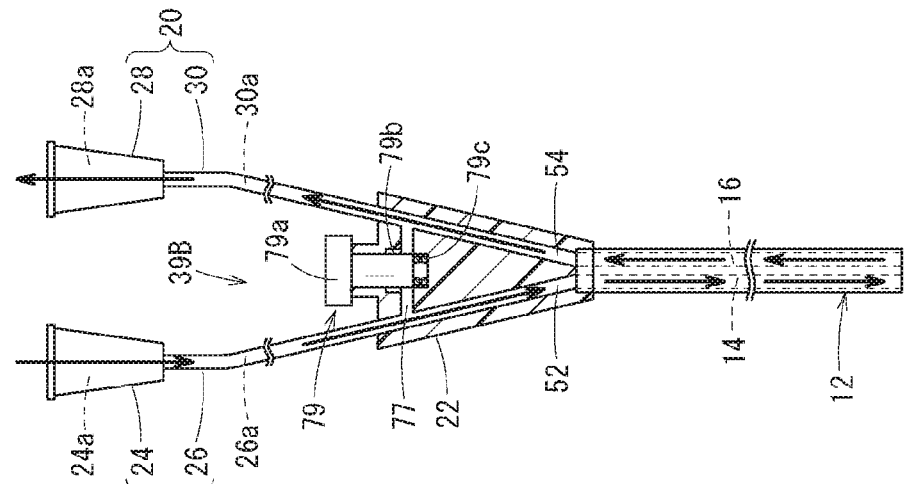
FIG. 8A is a cross-sectional view illustrating a first switching state of a switching mechanism part according to a second modified embodiment.
Figure 8B:
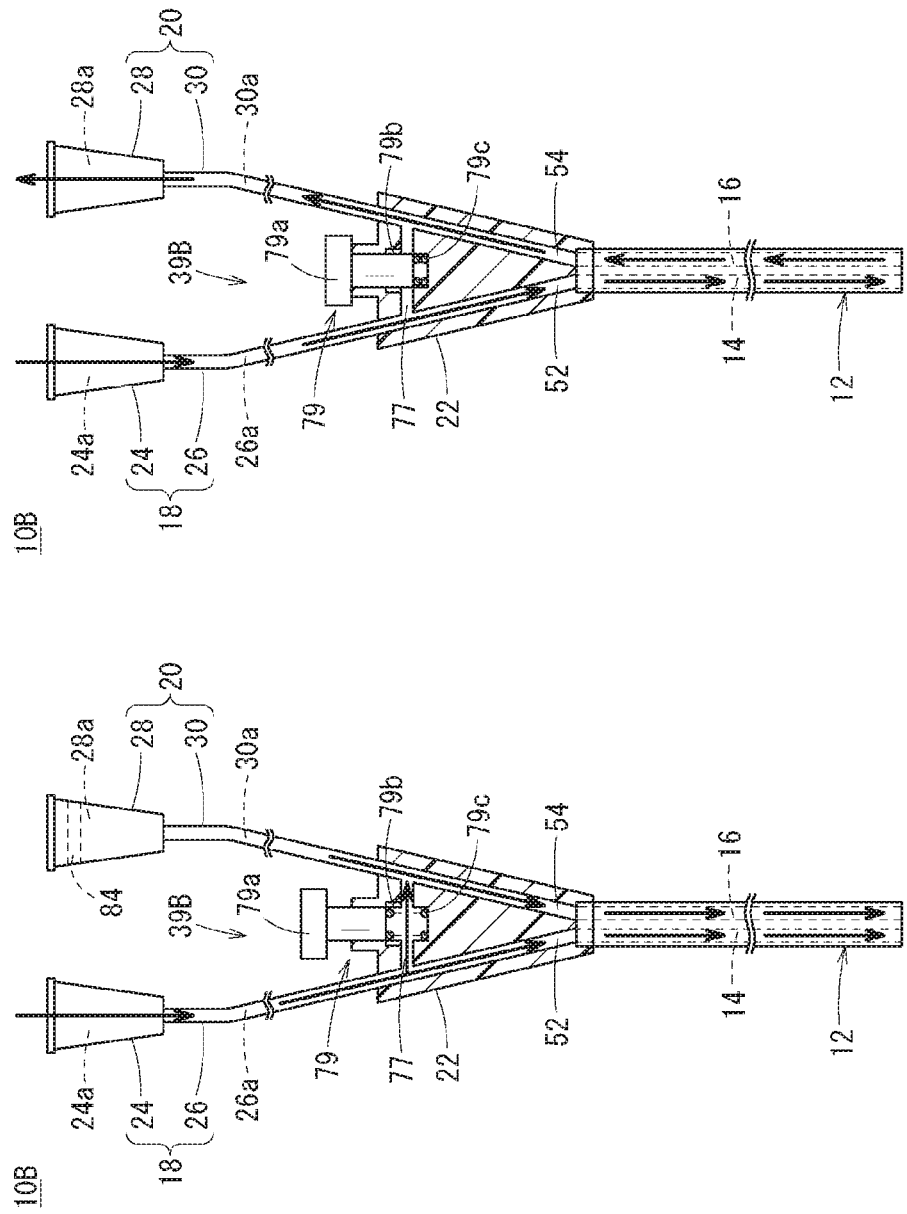
FIG. 8B is a cross-sectional view illustrating a second switching state of the switching mechanism part according to the second modified embodiment.

A switching mechanism part 39B according to a second modified embodiment illustrated in FIGS. 8A and 8B is different from the switching mechanism parts 38A, 38B and 39A in that the switching mechanism part 39B has a pin member 79a inserted into a hub 22 and the pin member 79a constitutes a knocking mechanism 79 together with an internal mechanism provided in the hub 22. The knocking mechanism 79 has a cam 79b and a spring 79c, and a known configuration in which in the case of pressing the pin member 79a once, the pin member 79a is locked inside the hub 22, and in the case of pressing the pin member 79a again, the pin member 79a is pushed outward from the hub 22 can be adopted.

Further, the switching mechanism part 39B can switch communication or non-communication of the communication path 77 depending on a position of the pin member 79a. That is, a first switching state is established by locking the pin member 79a at a position at which the pin member 79a has advanced into the hub 22, and a second switching state is established by locking the pin member 79a at a position at which the pin member 79a retreats to the outside of the hub 22.

Further, a switching mechanism part 39C according to a third modified embodiment illustrated in FIGS. 9A and 9B is different from the switching mechanism parts 38A, 38B, 39A and 39B in that a slide body 88 having a communication path 88a is provided to be movable relative to a hub 22. That is, the slide body 88 allows a first port 18 and a second lumen 16 to communicate with each other by exhibiting a first switching state in which the communication path 88a faces a first path 52 (or a first conduction path 26a) and a second path 54 (or a second conduction path 30a). Therefore, the switching mechanism part 39C can allow a liquid in the first port 18 to flow even toward the second lumen 16, thereby making it possible to suppress the blood from being introduced into the second lumen 16.

Further, the slide body 88 blocks communication between the first path 52 (the first port 18) and the second path 54 (the second lumen 16) by exhibiting a second switching state in which the slide body 88 moves relative to the hub 22 to displace the communication path 88a. Therefore, the liquid of the first port 18 can be allowed to flow to only the first lumen 14, and the liquid of the second port 20 can be allowed to flow to only the second lumen 16.

Third Embodiment

Figure 10A:
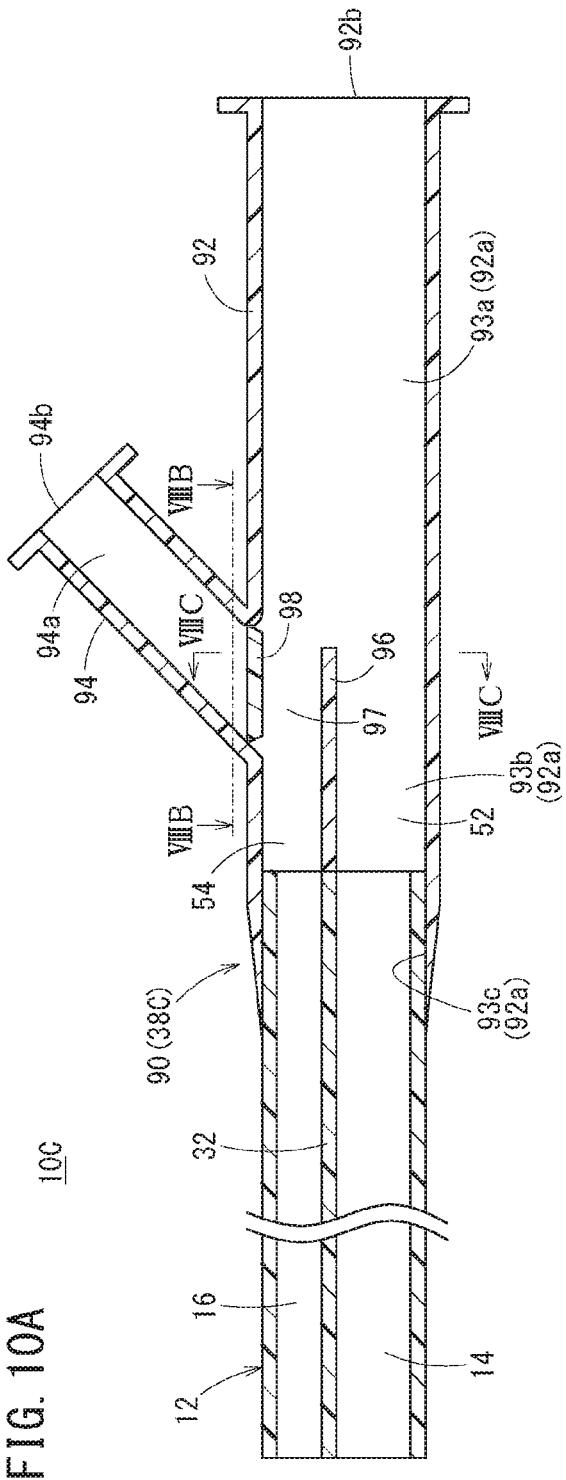
FIG. 10A is a cross-sectional view illustrating a first switching state of a catheter according to a third embodiment.

A catheter 10C according to the third embodiment is different from the above-mentioned catheters 10A and 10B in that the catheter 10C does not include the first tube 26, the first terminal 24, the second tube 30 and the second terminal 28 but a hub 90 is simply connected to a base end of a catheter body 12 as illustrated in FIG. 10A.

In this case, the hub 90 includes a hub body 92 linearly extended along an axial center of the catheter body 12; and a branch port 94 connected to an outer peripheral surface of the hub body 92 to constitute a switching mechanism part 38C. Further, abase end side of the hub body 92 rather than the branch port 94 serves as the first port 18, and the branch port 94 serves as the second port 20.

More specifically, the hub body 92 is formed as a tube body having a hollow part 92a therein, and a base end opening 92b communicating with the hollow part 92a is formed in the base end portion thereof. For example, in the base end side of the hub body 92, a connector of a medical instrument is inserted into the base end opening 92b into the hollow part 92a, and the base end side of the hub body 92 serves as a terminal for fixing the medical instrument.

The hollow part 92a has different functional spaces (a common space part 93a, a divided space part 93b and a mounting part 93c) along an axial direction of the hub body 92. The common space part 93a is formed in a circular cross-sectional shape by an inner peripheral surface of the hub body 92 to have a relatively large flow channel cross-sectional area, and a liquid is introduced thereinto from the medical instrument connected to the hub body 92.

The divided space part 93b is a portion formed of a front end of the common space part 93a and providing two paths (a first path 52 and a second path 54) by dividing the hollow part 92a into two parts using a partition wall 96. The partition wall 96 is positioned at the same position as that of a partition wall 32 of the catheter body 12 in a state in which the catheter body 12 is mounted, and extends in a short section of the divided space part 93b in the axial direction. Further, the first path 52 is provided in a lower side (a side opposite to a connection site of the branch port 94) in FIG. 10A, and the second path 54 is provided in an upper side (a connection site side of the branch port 94) in FIG. 10A, and the first and second paths 52 and 54 are linearly extended.

The mounting part 93c is a portion into which the catheter body 12 is inserted and fixedly maintained by a suitable fixation unit. In a state in which the hub body 90 and the catheter body 12 are fixed to each other, the first path 52 and a first lumen 14 communicate with each other, and the second path 54 and a second lumen 16 communicate with each other. Further, in this fixation state, it is preferable that a front end of the partition wall 96 and a base end of the partition wall 32 are liquid-tightly fixed to each other.

On the other hand, the branch port 94 is formed to obliquely protrude from a predetermined position on the outer peripheral surface of the hub body 92 (a position opposed to a base end side of the second path 54) in a direction toward the base end. The branch port 94 is formed in a cylindrical shape to be narrower than the hub body 92, and a branch space 94a is formed therein. Further, a base end opening 94b communicating with the branch space 94a is provided in a base end surface. Further, a connector 99 of another medical instrument administering a different liquid from the medical instrument connected to the hub body 92 is connected to the branch port 94.

Figure 10C:
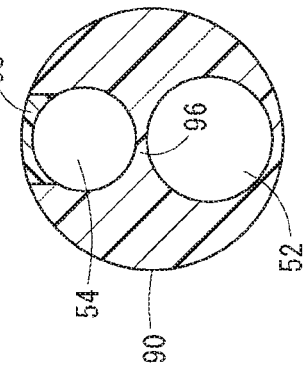
FIG. 10C is a cross-sectional view taken along lint XC-XC of FIG. 10A.
Figure 10B:
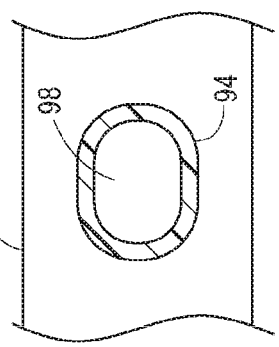
FIG. 10B is a cross-sectional view taken along line XB-XB of FIG. 10A.

A shutoff valve 98 is provided on a boundary between the branch port 94 and the hub body 92 (the outer peripheral surface of the hub body 92). As shown in FIGS. 10B and 10C, the shutoff valve 98 is formed in an oval shape along the outer peripheral surface of the hub body 92, and disposed between the hollow part 92a (the second path 54) and the branch space 94a in a general state in which the connector 99 is not inserted into the branch port 94. A circumferential part of the shutoff valve 98 is formed to be elastically deformable (elastically expandable and contractible), and liquid-tightly closes the space between the hub body 92 and the branch port 94.

Figure 11:
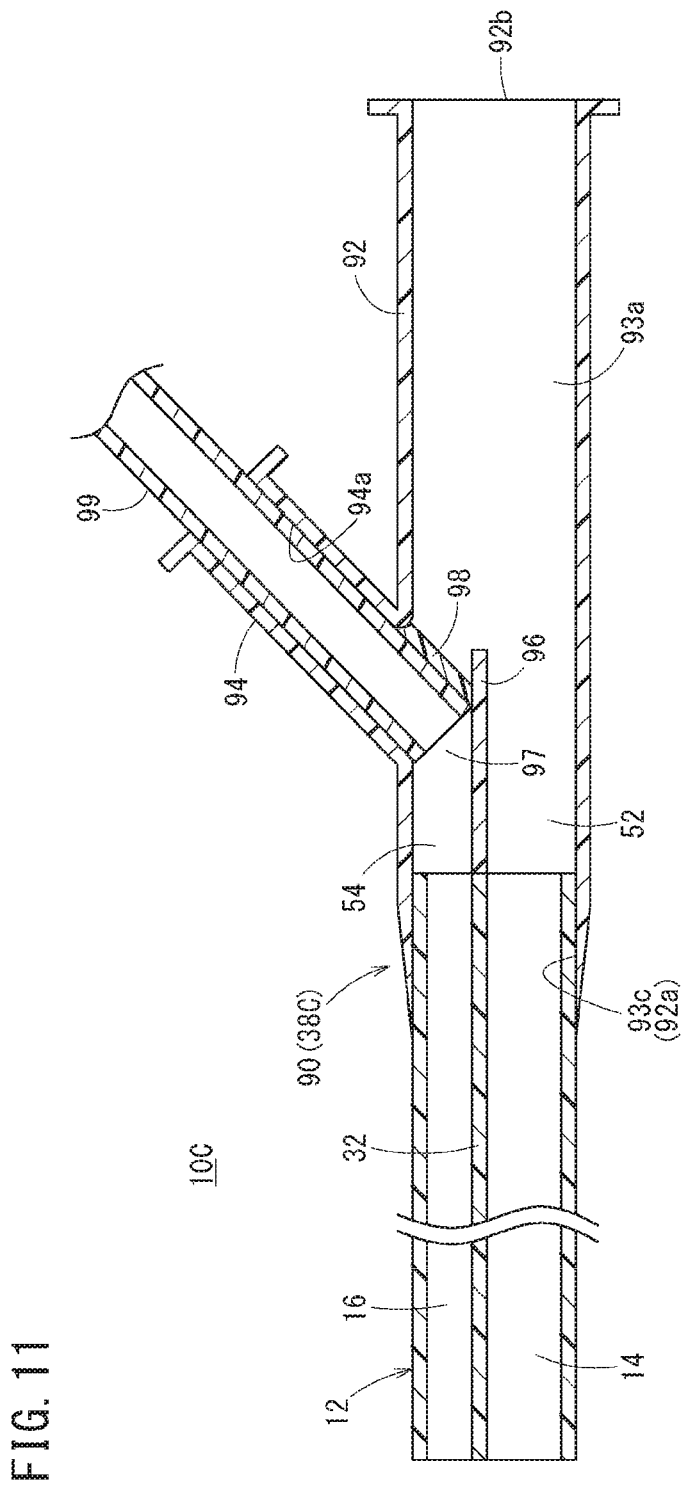
FIG. 11 is a cross-sectional view illustrating a second switching state of the catheter of FIG. 10A.

The connector 99 mounted in the branch port 94 is inserted into the branch space 94a from the base end opening 94b to push out the shutoff valve 98 as illustrated in FIG. 11. In this way, the shutoff valve 98 advances toward the base end side of the second path 54 to liquid-tightly block the second path 54 and the common space part 93a from each other. That is, in the first switching state in which the second path 54 is not closed by the shutoff valve 98 (the connector 99 is not connected to the branch port 94), the base end side of the second path 54 constitutes a communication path 97 communicating with the first lumen 14 through the common space part 93a and the first path 52. This communication path 97 is closed by the shutoff valve 98 by inserting the connector 99 into the branch port 94, such that a second switching state is established. In this state, a liquid administered from the connector 99 is allowed to flow the second lumen 16 through the second path 54.

The catheter 10C according to the third embodiment is basically configured as described above, and functions and effects of the catheter 10C are described below.

As illustrated in FIG. 10A, the catheter 10C is in the first switching state by connecting a medical instrument (not illustrated) to the hub body 92 without connecting another medical instrument to the branch port 94. In this first switching state, the common space part 93a of the hub body 92 communicates with the first path 52 and the second path 54 (communication path 97) of the divided space part 93b, respectively. Therefore, a portion of the liquid introduced into the common space part 93a from the medical device is introduced into the first lumen 14 through the first path 52 and flows in the first lumen 14 to thereby be administered to a patient. Further, a portion of the liquid introduced into the common space part 93a is introduced into the second lumen 16 through the second path 54 and flows in the second lumen 16 to thereby be administered to the patient. Here, the shutoff valve 98 blocks a space between the second path 54 and the branch space 94a, thereby preventing the liquid from leaking to the branch space 94a.

Therefore, the catheter 10C can suppress an inconvenience such as introduction of blood into the second lumen 16, coagulation of the introduced blood, or the like, by allowing the liquid to flow from the common space part 93a of the hub body 92 to the second lumen 16 even in the case in which the branch port 94 is not used.

Meanwhile, the catheter 10C is in the second switching state as illustrated in FIG. 11 by connecting the connector 99 of another medical instrument to the branch port 94 while connecting the medical instrument (not illustrated) to the hub body 92. In this second switching state, the shutoff valve 98 is elastically deformed to the second path 54 (communication path 97) side by the connector 99 inserted into the branch port 94, thereby blocking the space between the common space part 93a and the second path 54.

Therefore, the common space part 93a of the hub body 92 communicates with only the first path 52, and the liquid introduced into the common space part 93a from the medical instrument flows entirely to the first path 52 and the first lumen 14 to thereby be administered to the patient. Further, the liquid introduced into the second path 54 from the connector 99 of the medical instrument flows to the second path 54 and the second lumen 16 to thereby be administered to the patient. Here, the shutoff valve 98 can satisfactorily prevent the liquid from being introduced into the common space part 93a from the second path 54.

As described above, the catheter 10C according to the third embodiment can also obtain the same effects as those of the catheters 10A and 10B. Particularly, this catheter 10C includes the shutoff valve 98 in the hub 90. Therefore, a user of the catheter 10C can open and close the shutoff valve 98 by inserting the connector 99 of the medical instrument into the branch port 94 and more easily perform the switching between the first and second switching states of the catheter 10C.

Fourth Embodiment

A catheter 10D according to the fourth embodiment is different from the above-mentioned catheters 10A to 10C in that a hub 100 is connected and fixed to a base end of a catheter body 12, and this hub 100 constitutes a switching mechanism part 38D including a dedicated tubular port 104 connected to another medical instrument as illustrated in FIGS. 12, 13A, 13B and 14.

The hub 100 includes a hub body 102 linearly extended along an axial center of the catheter body 12; the tubular port 104 integrally formed in a direction orthogonal to an axial line of the hub body 102; and a side piece part 106 wrapping around an outer peripheral surface of the tubular port 104. Further, in the hub 100, a base end side of the hub body 102 rather than the tubular port 104 serves as the first port 18, and the tubular port 104 serves as the second port 20.

More specifically, the hub body 102 has a hollow part 102a in the inside in the base end side thereof rather than the tubular port 104, and is formed as a tapered tube body of which an end becomes thinner in a front end direction. A base end opening 102b communicating with the hollow part 102a is provided in a base end portion of the hub body 102. In this way, in the base end side of the hub body 102, a connector of a medical instrument (not illustrated) is inserted from the base end opening 102b into the hollow part 102a, and the base end side of the hub body 102 serves as a terminal for fixing the medical instrument.

Further, first and second paths 52 and 54 are provided in the inside in a front end side of the hub body 102 rather than the tubular port 104. The first and second paths 52 and 54 are extended in parallel with each other in an axial direction of the hub body 102. Further, front ends of the first and second paths 52 and 54 liquid-tightly communicate with first and second lumens 14 and 16 of the catheter body 12 inserted into and fixed to a front end of the hub body 102, respectively.

The tubular port 104 is formed in cylindrical shape having a relatively large diameter (thicker than the hub body 102 in the vicinity of a connection site), and protrudes relatively farther with respect to the outer peripheral surface of the hub body 102. An accommodation space 104a for accommodating a valve body 108, a displacement member 110 and a spring 112 is provided in the tubular port 104. An opening 104b communicating with the accommodation space 104a is provided in a first end portion (an upper end portion in FIG. 12) of the tubular port 104, and a connector 99 of another medical instrument can be inserted into the accommodation space 104a. An inner peripheral surface constituting the accommodation space 104a is formed to have a constant inner diameter in a lower side, but the diameter thereof is gradually decreased from a middle portion of the accommodation space 104a to the opening 104b on an upper side. Further, the accommodation space 104a communicates with a front end of the hollow part 102a in the connection site between the tubular port 104 and the hub body 102.

The valve body 108 is formed in a tubular shape and accommodated in the accommodation space 104a in a state in which the displacement member 110 is mounted in a lower end portion of the valve 108. The valve body 108 is disposed to be slidable in an axial direction of the accommodation space 104a. An exterior of the valve body 108 is formed in a conical shape at an upper side so as to coincide with an inner peripheral surface on the upper side of the accommodation space 104a, and comes in liquid-tight contact with an inner peripheral surface of the tubular port 104. A closing film 109 is provided on an upper end portion of the valve body 108, and a slit 109a capable of communicating with a flow channel 114 provided in the valve body 108 is formed in the closing film 109. The flow channel 114 extends downward from the closing film 109 of the valve body 108 in the axial direction and bent at a position having a predetermined height, thereby communicating with a valve hole part 108a formed in an outer peripheral surface of the valve body 108. The valve hole part 108a is set to communicate with the second path 54 in a connection state in which the connector 99 is inserted into the tubular port 104 (see FIG. 14).

Further, a groove part 116 corresponding to a communication path is formed in the outer peripheral surface of the valve body 108 at a position having a predetermined height (a position lower than the valve hole part 108a) by cutting the valve body 108 inward. The groove part 116 is provided to wrap halfway around the outer peripheral surface of the valve body 108 in a circumferential direction in across-sectional view orthogonal to an axial direction of the valve body 108 (in a plan view of the hub 100, see FIG. 13B).

In a general state (first switching state) in which the connector 99 is not inserted into the tubular port 104, an upper end portion of the valve body 108 is inserted into the opening 104b, such that the closing film 109 is exposed so as to be flush with an upper surface of the tubular port 104. Further, in this general state, a base end of the groove part 116 communicates with the hollow part 102a of the hub body 102, and a front end of the groove part 116 is disposed at a position at which the front end communicates with the second path 54.

The displacement member 110 is formed in a disk shape and configured as a seat that supports the valve body 108 on one side and receives the spring 112 on the other side. Further, the spring 112 is accommodated on a lower end portion (bottom portion) of the tubular port 104 and applies an energizing force for energizing the displacement member 110 in an upward direction. Therefore, when valve body 108 is pushed by the connector 99 and is displaced downward, the spring 112 is elastically contracted, thereby allowing the connection state (second switching state). Further, when the connector 99 is removed, the spring 112 elastically restores to dispose the valve body 108 at a position in the general state.

The side piece part 106 provided on a side peripheral surface of the tubular port 104 is connected to the hub body 102 in the base end side and the front end side rather than the tubular port 104, such that the side piece part 106 is formed to protrude to a side of the hub body 102. A side path 118 communicating between the hollow part 102a and the first path 52 is provided in the side piece part 106. This side path 118 is formed in a semicircular shape in which the side path 118 just wraps around the outside of the tubular port 104 just in a plan view (see FIG. 13B). Therefore, the hub 100 has a configuration in which the hollow part 102a, the side path 118 and the first path always communicate with each other.

Therefore, in the general state in which the valve body 108 is placed at an upper position, the groove part 116 communicating with the hollow part 102a can communicate with the first lumen 14 of the catheter body 12 through the hollow part 102a, the side path 118 and the first path 52.

The catheter 10D according to the fourth embodiment is basically configured as described above, and functions and effects thereof are described below.

Figure 13A:
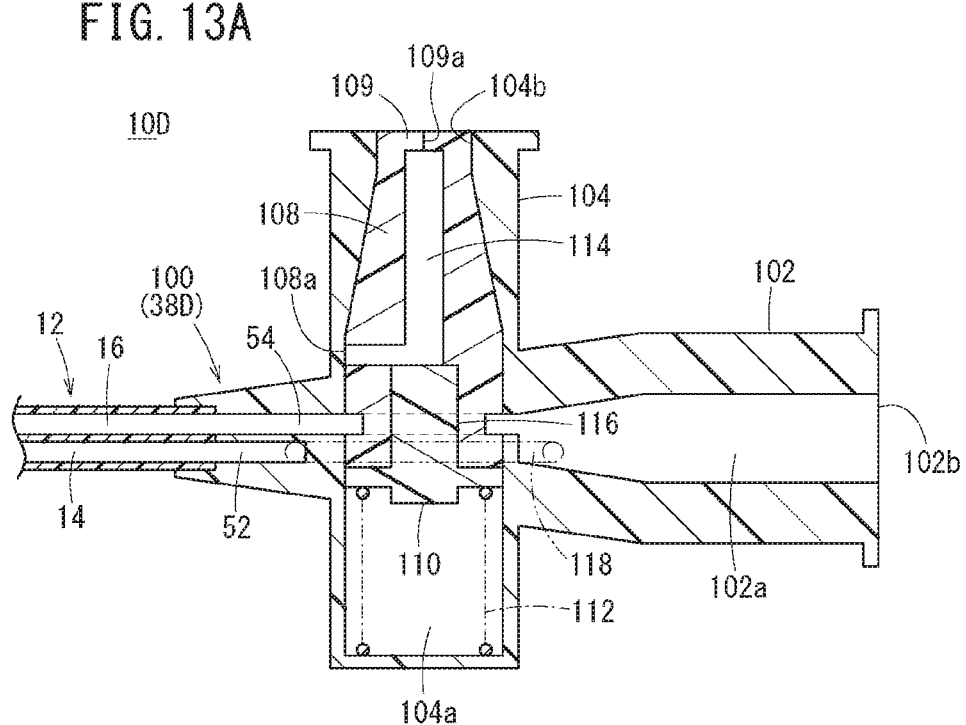
FIG. 13A is a side cross-sectional view illustrating a first switching state of the catheter of FIG. 12.
Figure 13B:
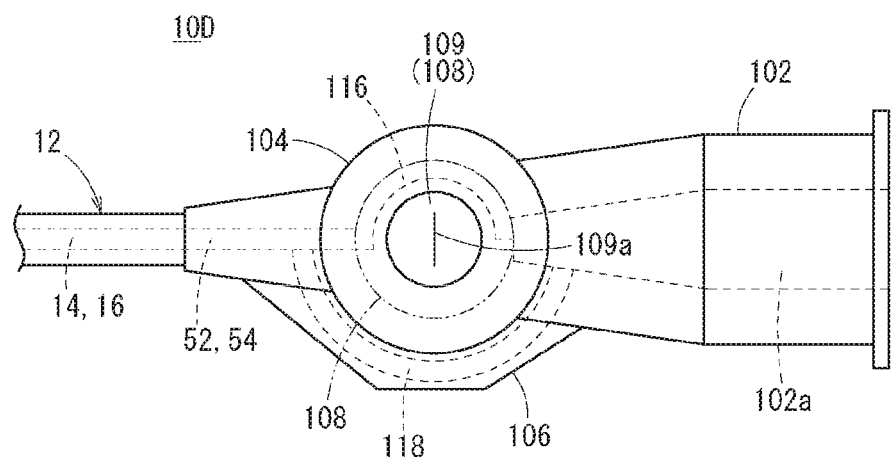
FIG. 13B is a plan view of the catheter of FIG. 13A.

As illustrated in FIG. 13A, the catheter 10D is in the first switching state by connecting the connector of the medical instrument (not illustrated) to the hub body 102 without using the tubular port 104. In this first switching state, the valve body 108 is energized by the spring 112 to thereby be disposed at the upper position in the tubular port 104, thereby allowing the groove part 116 to communicate with the hollow part 102a and the second path 54. Therefore, a portion of the liquid flowing out from the connector to the hollow part 102a flows to the second lumen 16 through the hollow part 102a, the groove part 116 and the second path 54. At the same time, because the hollow part 102a, the side path 118 and the first path 52 communicate with each other in the hub body 102, a portion of the liquid is allowed to flow from the connector of the hub body 102 to the first lumen 14.

Therefore, the catheter 10D can suppress an inconvenience such as introduction of blood into the second lumen 16, coagulation of the introduced blood, or the like, by allowing the liquid to flow from the hollow part 102a to the second lumen 16 through the groove part 116 even in the case in which the tubular port 104 is not used.

Figure 14:
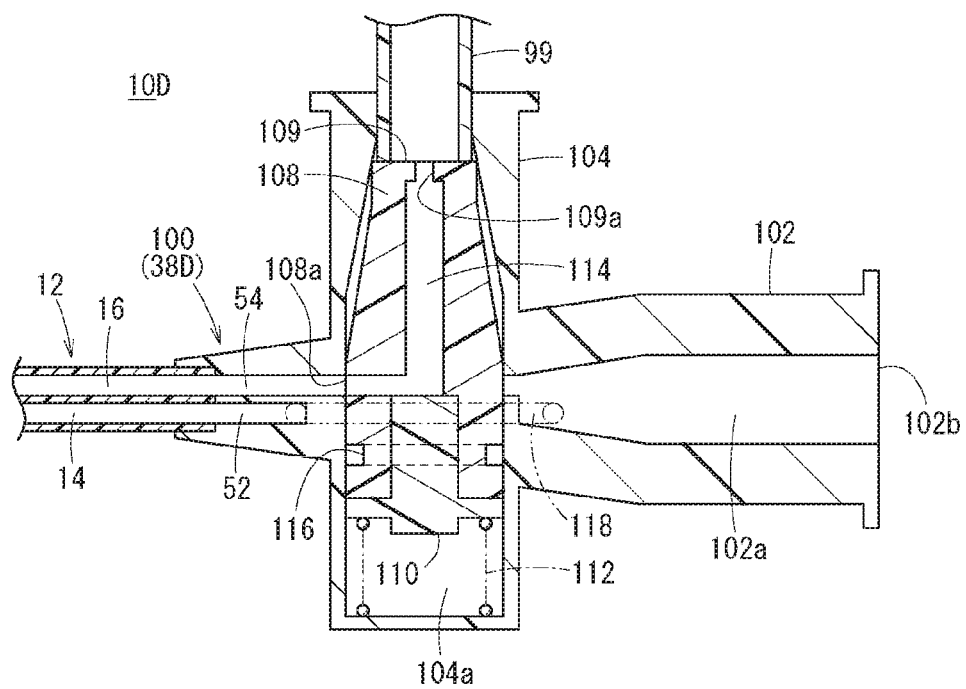
FIG. 14 is a side cross-sectional view illustrating a second switching state of the catheter of FIG. 12.

Meanwhile, the catheter 10D is in the second switching state as illustrated in FIG. 14 by connecting the connector 99 of another medical instrument to the tubular port 104 while connecting the connector of the medical instrument (not illustrated) to the hub body 102. In this second switching state, the valve body 108 is displaced downward in the accommodation space 104a by the connector 99 inserted into the tubular port 104 from the opening 104b, such that the valve hole part 108a faces the second path 54. In this case, the outer peripheral surface of the valve body 108 displaces the groove part 116 downward, thereby closing the connection site between the hollow part 102a and the accommodation space 104a. In addition, the closing film 109 of the valve body 108 is configured so that the slit 109a is opened by a press of the connector 99, thereby allowing the flow channel 114 of the valve body 108 and the inside of the connector 99 to communicate with each other.

As described above, the valve body 108 is displaced in the tubular port 104, such that the hollow part 102a of the hub body 102 communicates with only the first path 52. Therefore, the liquid introduced into the hollow part 102a from the connector of the medical instrument is flows entirely in the side path 118, the first path 52 and the first lumen 14 to thereby be administered to a patient. Further, the liquid introduced into the flow channel 114 in the valve body 108 from the connector 99 of another medical instrument flows out from the valve hole part 108a to the second path 54 to thereby be administered to the patient through the second lumen 16.

As described above, the catheter 10D according to the fourth embodiment can also obtain the same effects as those of the catheters 10A to 10C. Particularly, in the catheter 10D, because the valve body 108 has the groove part 116 (communication path), when the connector 99 is inserted into the tubular port 104, the groove part 116 can be opened and closed by moving the valve body 108. Therefore, in the catheter 10D, the first and second switching states can be more easily switched. Further, because the valve body 108 has the flow channel 114 that allows the second port 20 and the second lumen 16 to communicate with each other, the liquid can be directly supplied to the flow channel 114 in a state in which the connector 99 is inserted into the second port 20. Therefore, it is possible to allow the liquid to satisfactorily flow to the second lumen 16 through the flow channel 114 in the valve body 108.

Further, a modified example of the catheter 10D may have a configuration in which the side path 118 (side piece part 106) is not provided in the hub body 102, and a plurality of groove parts are formed on the outer peripheral surface of the valve body 108 to switch arrangement of the plurality of grooves parts depending on displacement of the valve body 108. For example, a first switching state groove part communicating with the first path 52 is formed on the outer peripheral surface of the valve body 108 in a side opposite to the groove part 116 in the circumferential direction, and a second switching state groove part may be formed on the outer peripheral surface of the valve body 108 at a position where the valve hole part 108a faces the second path 54. In this way, even though the valve body 108 is displaced, the hollow part 102a and the first path 52 always communicate with each other.

Fifth Embodiment

As illustrated in FIGS. 15A and 15B, a catheter 10E according to the fifth embodiment is different from the above-mentioned catheters 10A to 10D in that a hub 120 (switching mechanism part 38E) connected to a base end of a catheter body 12 is configured as a Y-shaped connector.

This hub 120 includes a catheter terminal 122 for mounting the catheter body 12; a first terminal 124 connected to be obliquely inclined with respect to the catheter terminal 122; and a second terminal 126. Further, a first path 52, a second path 54 and a communication path 128 are formed in the hub 120, and a valve body 130 is provided in the second terminal 126.

The catheter terminal 122 includes a mounting hole 47 into which the base end of the catheter body 12 is inserted and fixed. In the catheter body 12, in a state in which the hub 120 is mounted, the first lumen 14 communicates with the first path 52, and a second lumen 16 communicates with the second path 54.

The first terminal 124 is formed in a tubular shape in which the first path 52 is included, and has a first opening 124a communicating with the first path 52 at a first end portion thereof. A connector of a medical instrument (not illustrated) is inserted into the first opening 124a, and a liquid is administered from the connector. The first path 52 reaches the mounting hole 47 from the first terminal 124 through a central portion of the hub 120, and is formed to have a relatively large diameter at an upstream side thereof.

The second terminal 126 is formed in a tubular shape in which the second path 54 is included therein, and has a second opening 126b communicating with the second path 54 at a first end portion thereof. A connector 99 of another medical instrument is inserted into the second opening 126b, and a liquid is administered from the connector 99. The second path 54 reaches the mounting hole 47 from the second terminal 126 through the central portion of the hub 120, and a valve disposition space 129 slidably accommodating the valve body 130 therein is formed in an upstream side portion of the second path 54. An inner peripheral surface of the hub 120 constituting the valve disposition space 129 is formed in a tapered shape in which a diameter thereof is gradually decreased toward the center portion of the hub 120.

The communication path 128 communicates between an upstream side portion of the first path 52 and the valve disposition space 129. Therefore, the communication path 128 is configured as a path capable of allowing the first and second lumens 14 and 16 to communicate with each other.

The valve body 130 protrudes from the second opening 126b into the valve disposition space 129, and a support film 132 connected to an inner surface of the valve disposition space 129 is formed on an outer peripheral surface thereof. The valve body 130 has a cylindrical shape, and a front end portion thereof is formed in a tapered shape matching the inner peripheral surface of the hub 120 constituting the valve disposition space 129. A flow channel 134 is provided in the valve body 130 along an axial direction of the valve body 130. The flow channel 134 communicates with a valve hole part 130a at a front end of the valve body 130 and communicates with a slit 131a of a closing film 131 provided at a base end of the valve body 130. The slit 131a is closed in a state in which the closing film 131 of the valve body 130 is positioned in the second opening 126b, and is opened by being pushed by the connector 99 of the medical instrument.

The catheter 10E according to the fifth embodiment is basically configured as described above, and functions and effects thereof are described below.

As illustrated in FIG. 15A, the catheter 10E is in a first switching state by connecting the connector of the medical instrument (not shown) to the first terminal 124 without using the second terminal 126. In this first switching state, the valve body 130 is present at an upper position of the valve disposition space 129 (at the second opening 126*b* side), and at a front end side of the valve disposition space 129, a communication site between the communication path 128 and the second path 54 is opened. Therefore, the hub 120 allows a portion of the liquid to flow from the connector to the first lumen 14 through the first path 52. At the same time, the hub 120 allows a portion of the liquid to flow from the connector to the second lumen 16 through the first path 52, the communication path 128 and the second path 54.

Therefore, the catheter 10E can suppress an inconvenience such as introduction of blood into the second lumen 16, coagulation of the introduced blood, or the like, by allowing the liquid to flow to the second lumen 16 even in the case in which the medical instrument is not connected to the second terminal 126.

Meanwhile, the catheter 10E is in a second switching state as illustrated in FIG. 15B by connecting the connector 99 of another medical instrument to the second terminal 126 while connecting the connector of the medical instrument (not illustrated) to the first terminal 124. In this second switching state, the valve body 130 is displaced to an internal portion of the valve disposition space 129 by the connector 99 inserted into the second opening 126*b* to close a space between the communication path 128 and the second path 54. In addition, the closing film 131 of the valve body 130 allows the slit 131*a* to be opened by a press of the connector 99, thereby allowing the flow channel 134 of the valve body 130 and the inside of the connector 99 to communicate with each other.

The valve body 130 is displaced in the second terminal 126 to block communication between the second path 54 and the first lumen 14, so that the liquid flowing in from the first terminal 124 flows entirely to the first path 52 and the first lumen 14 to thereby be administered to a patient. Further, the liquid introduced into the flow channel 134 in the valve body 130 from the second terminal 126 flows from the valve hole part 130*a* to the second path 54 and the second lumen 16 to thereby be administered to the patient.

Further, in the catheter 10E, as a fourth modified embodiment illustrated in FIGS. 16A and 16B, a front end portion of a valve body 140 may be formed in a hemi-spherical shape, and at the same time, a valve disposition space 142 may be formed in a hemispherical inner surface coinciding with the front end portion of the valve body 140. In this way, a front end side of the valve body 140 is allowed to come in surface-contact with an inner side of the valve disposition space 142 in a wide range in a state in which the connector 99 of the medical instrument is inserted, such that a communication path 128 can be more reliably closed. In short, a mechanism (switching mechanism part 38E) for closing the communication path 128 is not particularly limited, and various configurations capable of blocking communication between the second path 54 and the first lumen 14 may be adopted.

Further, in a hub 120 according to the fourth modified embodiment, the second path 54 is formed to have a small flow channel cross sectional area, and a liquid can be allowed to flow to the second lumen 16 by decreasing a flow amount of the liquid.

As described above, the catheter 10E according to the fifth embodiment can also obtain the same effects as those of the catheters 10A to 10D. Particularly, in the catheter 10E, the valve body 130 or 140 is provided to be displaceable in the valve disposition space 129 of the hub 120, and the catheter 10E can allow the liquid to smoothly flow from the first port 18 to the second lumen 16 by opening the communication path 128 in a standby state (the first switching state). Meanwhile, the catheter 10E can more surely block communication between the first port 18 and the second lumen 16 by closing the communication path 128 in a connection state (the second switching state).

The present invention is not limited to the embodiments described above, and various modifications are possible without departing from the gist of the present invention.

What is claimed is:
1. A catheter comprising:
   a first port that is connectable to a connector of a first medical instrument;
   a second port that is connectable to a connector of a second medical instrument;
   a first lumen;
   a second lumen; and
   a switching mechanism part selectively switchable between:
      a first switching state in which (i) the first port is configured to receive liquid from the first medical instrument and to provide the liquid to the first lumen and the second lumen, and (ii) communication between the second port and the second lumen is blocked, and
      a second switching state in which (i) the first port is configured to receive liquid from the first medical instrument and to provide the liquid to the first lumen, (ii) the second port is configured to receive liquid from the second medical instrument and to provide the liquid to the second lumen, and (iii) communication between the first port and the second lumen is blocked.
2. The catheter according to claim 1, wherein:
   the switching mechanism part comprises a communication path configured to selectively communicate between the first lumen and the second lumen, and
   in the second switching state, the communication path is closed.
3. The catheter according to claim 2, wherein:
   the switching mechanism part comprises a valve body configured to selectively open and close the communication path.
4. The catheter according to claim 3, wherein
   the switching mechanism part comprises:
      a body part; and
      the valve body, which comprises the communication path and is configured to be displaceable in the body part,
   the valve body causes the catheter to be in the first switching state by opening the communication path in a standby state in which a connector is not inserted into the second port, and
   the valve body causes the catheter to be in the second switching state by moving the communication path relative to the body part so as to close the communication path in an insertion state in which the connector is inserted into the second port.
5. The catheter according to claim 4, wherein:
   the valve body comprises a flow channel that allows the second port and the second lumen to communicate with each other in the insertion state.
6. The catheter according to claim 3, wherein
   the switching mechanism part comprises:
      a body part comprising the communication path therein; and the valve body configured to be displaceable in the body part, the valve body causes the catheter to be in the first switching state by opening the communication path in a standby state in which a connector is not inserted into the second port, and the valve body causes the catheter to be in the second switching state by closing the communication path in an insertion state in which the connector is inserted into the second port.

7. The catheter according to claim 6, wherein:
the valve body comprises a flow channel that allows the second port and the second lumen to communicate with each other in the insertion state.

8. The catheter according to claim 1, wherein:
the switching mechanism part comprises a communication path configured to selectively communicate between the first lumen and the second lumen, and in the second switching state, the communication path is moved relative to the first switching state.

9. The catheter according to claim 1, wherein
the switching mechanism part comprises:
 a body part; and
 a rotation part mounted to be rotatable on the body part between the first switching state and the second switching state, the rotation part comprising a communication path therein,
in the first switching state, the rotation part is oriented such that the first port and the second lumen communicate with each other via the communication path, and
in the second switching state, the rotation part is oriented such that the second port and the second lumen communicate with each other via the communication path.

10. The catheter according to claim 1, wherein:
at least one part of the first lumen and at least one part of the second lumen extend in parallel with each other.

11. The catheter according to claim 10, wherein:
the at least one part of the first lumen and the at least one part of the second lumen extend in parallel with each other in an axial direction of a catheter body.

12. A switching device comprising:
a body part comprising:
 a first insertion hole that is connectable to a connector of a first medical instrument,
 a second insertion hole that is connectable to a connector of a second medical instrument,
 a first path, and
 a second path; and
a rotation part selectively switchable between:
 a first switching state in which (i) the first insertion hole is configured to receive liquid from the first medical instrument and to provide the liquid to the first path and the second path, and (ii) communication between the second insertion hole and the second path is blocked, and
 a second switching state in which (i) the first insertion hole is configured to receive liquid from the first medical instrument and to provide the liquid to the first path, (ii) the second insertion hole is configured to receive liquid from the second medical instrument and to provide the liquid to the second path, and (iii) communication between the first insertion hole and the second path is blocked.

13. The switching device according to claim 12, wherein:
the first path is located in the body part; and
the second path is located in the body part.

14. A method for operating a catheter, the method comprising:
providing a catheter comprising:
 a first port,
 a second port,
 a first lumen,
 a second lumen, and
 a switching mechanism part selectively switchable between a first switching state and a second switching state;
switching the switching mechanism part to the first switching state, in which (i) a first liquid flows from the first port into the first lumen and the second lumen, and (ii) a second liquid is prevented from flowing from the second port into the second lumen; and
switching the switching mechanism part to the second switching state, in which (i) the first liquid flows from the first port into the first lumen, (ii) the second liquid flows from the second port into the second lumen, and (iii) the first liquid is prevented from flowing from the first port into the second lumen.

\* \* \* \* \*